(12) United States Patent
Ashweek et al.

(10) Patent No.: US 10,138,214 B2
(45) Date of Patent: Nov. 27, 2018

(54) SUBSTITUTED TRIAZOLES AND METHODS RELATING THERETO

(71) Applicant: Neurocrine Biosciences, Inc., San Diego, CA (US)

(72) Inventors: Neil J. Ashweek, San Diego, CA (US); John P. Williams, San Diego, CA (US); Deborah Slee, Cardiff, CA (US); Manisha Moorjani, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 0 days.

(21) Appl. No.: 15/630,225

(22) Filed: Jun. 22, 2017

(65) Prior Publication Data

US 2017/0349558 A1    Dec. 7, 2017

Related U.S. Application Data

(62) Division of application No. 15/010,925, filed on Jan. 29, 2016, now Pat. No. 9,718,789.

(60) Provisional application No. 62/259,314, filed on Nov. 24, 2015, provisional application No. 62/110,415, filed on Jan. 30, 2015.

(51) Int. Cl.

| | |
|---|---|
| C07D 249/04 | (2006.01) |
| C07D 405/04 | (2006.01) |
| C07D 401/12 | (2006.01) |
| C07D 413/04 | (2006.01) |
| C07D 403/04 | (2006.01) |
| A61K 31/5377 | (2006.01) |
| A61K 31/4192 | (2006.01) |
| A61K 31/422 | (2006.01) |

(52) U.S. Cl.
CPC .......... *C07D 249/04* (2013.01); *C07D 401/12* (2013.01); *C07D 403/04* (2013.01); *C07D 405/04* (2013.01); *C07D 413/04* (2013.01)

(58) Field of Classification Search
CPC ............ A61K 31/5377; A61K 31/4192; A61K 31/422; C07D 249/04; C07D 401/12; C07D 403/04; C07D 405/04; C07D 413/04

See application file for complete search history.

(56) References Cited

FOREIGN PATENT DOCUMENTS

| EP | 2752411 A1 | 7/2014 |
|---|---|---|
| WO | 2009/060053 A1 | 5/2009 |
| WO | 2014/106622 A1 | 7/2014 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL;http://www.cnn.com/2003/HEALTH/conditions/09/24/alzheimers.drug.ap/index.html>.*
Mandel et al., CNS Drugs, 2003: 17(10); 729-62.*
Lovelette et al., "Studies in Nonbridgehead Fused Nitrogen Heterocycles. Fused 1,2,3-Triazoles," *J. Org. Chem.*, 37(25): 4124-4128 (1972).

* cited by examiner

*Primary Examiner* — Rebecca L Anderson
(74) *Attorney, Agent, or Firm* — Seed IP Law Group LLP

(57) ABSTRACT

Substituted 1,2,3-triazole compounds are disclosed which have utility in the treatment of a variety of neurological disorders. The compounds provided herein have the general structure:

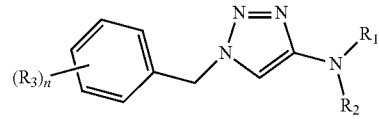

wherein $R_1$, $R_2$, $R_3$ and n are as defined herein, including stereoisomers, esters, solvates and pharmaceutically acceptable salts thereof. Also disclosed are compositions containing a compound provided herein in combination with a pharmaceutically acceptable carrier, as well as methods relating to the use thereof for treating neurological disorders in a subject in need thereof.

20 Claims, No Drawings

SUBSTITUTED TRIAZOLES AND METHODS RELATING THERETO

BACKGROUND

Technical Field

This disclosure relates generally to substituted 1,2,3-triazole compounds, to processes and intermediates used in their preparation, to compositions containing them and to methods of treating neurological disorders by administration of such compounds to a warm-blooded animal in need thereof.

Description of the Related Art

Essential tremor (ET) is one of the more common tremor disorders and one of the more common neurological diseases. While the disease is often called "benign", this postural and/or kinetic tremor frequently causes difficulty with everyday tasks such as writing, pouring and eating. ET has a prevalence comparable to that of epilepsy and greater than both Parkinson's disease and Alzheimer's disease. The incidence of ET rises with increasing age and a family history of ET appears to correlate with a younger onset of disease. Pharmacological treatments of this disorder are limited due to variable effectiveness, occurrence of side effects and lack of understanding of the pathophysiology of the disease.

ET has variable clinical expression characterized by a postural and/or kinetic tremor with a frequency range between 4 and 12 Hz. The tremor frequency generally decreases over time while amplitude increases. Approximately 90% of patients have tremor in their upper extremities, 30% have a head tremor, 20% voice tremor, 10% face or jaw tremor and 10% lower body tremor. Additionally, recent studies indicate higher rates of mild cognitive changes, depression, anxiety, social phobias and olfactory and hearing deficits in ET patients compared to normal controls (see, e.g., Zesiewicz et al., *Neuropsychiatric Disease and Treatment*, 2010:6, 401-408).

The oldest anti-tremorgenic agent in the management of ET is ethanol. While showing some beneficial effects, this therapy is impractical due to addiction issues and serious drawbacks with long-term ethanol use (see, e.g., Iseri et al., *Neuropharmacology*, 2011, 61:715-723).

Although many medications have been tested, the pharmacological treatment of ET is not optimal. Two medications are considered first-line treatments: propranolol, a nonselective beta blocker which is the only FDA approved agent for ET; and primidone, an antiepileptic drug. In addition to side effects which include bronchoconstriction, bradycardia, hypotension, depression and fatigue for propranolol and sedation, dizziness, fatigue, nausea and depression for primidone (see, e.g., Abboud et al., *Cleveland Clinic Journal of Medicine*, 2011 78:12:821-828), neither drug reduces tremor levels to asymptomatic levels nor is effective in more than about half of patients with disease.

In addition to the first-line treatments for ET noted above, over the last decade several other therapies have been studied, most of which are older drugs repurposed for ET such as antiepileptic agents, gabapentin, topiramate, zonisamide, levitiracetam, phenobarbital, pregabalin and lacosamide; calcium antagonists flunarizine and nicarpine; benzodiazepines such as alprazolam; antidepressant mirtazapine; and agents such as sodium oxybate, T-2000 and 1-octanol. Further botulinum toxin injection has been the subject of several small studies and may be useful for intractable head and voice tremor (see, e.g., Shill, *Clinical Medicine: Therapeutics* (2009) 1: 613-620, Sadeghi et al., *Drugs* 2010; 70(17):2215-2228).

Surgical procedures may also provide treatment for severe and refractory ET. Deep Brain Stimulation of the ventral intermediate thalamus involves surgery to implant an electrode and a pulse generator. Thalamotomy is a stereotactic procedure that creates a lesion in the ventral intermediate nucleus of the thalamus. Side effects and adverse events limit this surgery to patients who are not responsive to pharmacotherapy (see, e.g., Zesiewicz et al., *Neuropsychiatric Disease and Treatment*, (2010) 6:401-408).

Epilepsy is a brain disorder characterized by periodic and unpredictable seizures. The behavioral manifestations of epileptic seizures in human patients range from mild twitching of an extremity to loss of consciousness and uncontrollable convulsions. Up to 1% of the population is afflicted, making epilepsy one of the most common neurological problems and a considerable economic burden on society. Despite the considerable progress in our understanding of the pathophysiology and pharmacotherapy of seizures and epilepsy, the cellular basis of human epilepsy remains an enigma. In the absence of etiological understanding, approaches to pharmacotherapy have been directed to the control of symptoms; namely, the suppression of seizures. More concerning is that current antiepileptic drugs do not halt the underlying natural progression of the disorder.

Over the years, there has been considerable success in the development of novel antiepileptic drugs (AED) along with new improved formulations. These include older "first generation" drugs such as carbamazepine, phenobarbital, valproic acid and newer, "second generation" drugs such as lamotrigine, vigabatrin, tiagabine, topiramate, gabapentin and levetiracetam (see, e.g., Brazil et al., *Ann. Rev. Med.*, 1998, 49:135-162; McCabe P H., *Expert Opinion. Pharmacother.*, 2000, 1:633-674]. The selection of an antiepileptic drug for treatment is predicated on its efficacy for the specific type of seizures, tolerability and safety (see, e.g., Regesta et al., *Epilepsy Res.*, 1999, 34:109-122; Kwan et al., *Engl. J. Med.*, 2000, 342:314-319).

Status epilepticus (SE) is a life threatening condition characterized by a prolonged state of continuous convulsions resulting in significant morbidity and mortality. SE is defined as seizure activity lasting for 30 minutes or longer without regaining consciousness. Treatment should be initiated promptly since prolonged SE may result in death, progressive brain damage or develop into the difficult to treat refractory SE. As many as 200,000 people are affected in the U.S. annually, with as many as 55,000 deaths. Causes of SE include both acute health problems such as stroke, metabolic disturbances, infections, head trauma and drug interactions and chronic processes such as pre-existing epilepsy, discontinuation of drug therapy and central nervous system tumors (see, e.g., Deshpande et al., *Front Neurol* (2014, 5:11).

SE is categorized as convulsant or nonconvulsant, both of which require prompt treatment to prevent death and brain injury. The pathophysiology of SE is not clearly understood. After medical stabilization of the patient a first line treatment involves intravenous or intramuscular administration of a benzodiazepine such as midazolam, diazepam or lorazepam. Second line therapy involves the additional administration of phenytoin, fosphenytoin, phenobarbital or valproic acid. Approximately 40% of SE cases do not resolve to this treatment and are termed refractory. Refractory SE is generally treated with anesthetics such as propofol or phenobarbital. (see, e.g., Reddy et al., *Int. J. Mol. Sci.* 2013, 14:18284-318).

Nerve agents inhibit acetylcholinesterase resulting in elevated acetylcholine levels in the nervous system. Ensuing cardiorespiratory depression and status epilepticus may lead to death or brain damage in affected individuals (see, e.g., Apland et al., *J Pharmacol Exp Ther* 2013, 344:133-40).

While significant strides have been made in this field, a need remains for small molecules effective in the treatment of neurological disorders and diseases, especially essential tremor, epilepsy, status epilepticus, and/or nerve agent exposure. These small molecules may reduce some of the side effects and limitations of current drug therapies such as treatment of refractory patients, reduced sedation, cognitive and behavioral effects, drug/drug interactions, and teratogenicity/genotoxicity concerns. The present disclosure fulfills these needs and provides other related advantages.

BRIEF SUMMARY

In brief, this invention is generally directed to 1,2,3-triazole analogs, as well as to methods for their preparation and use, and to pharmaceutical compositions containing such compounds. More specifically, the 1,2,3-triazole analogs described herein are compounds having the following structure (A):

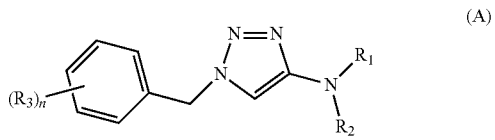

(A)

including stereoisomers, esters, solvates and pharmaceutically acceptable salts thereof, wherein $R_1$, $R_2$, $R_3$, and n are as defined herein.

In another embodiment, a pharmaceutical composition is provided comprising any one of the compounds described above and herein in combination with a pharmaceutically acceptable carrier and/or diluent.

In another embodiment, methods are provided for treating a condition in a subject in need thereof, wherein the condition is essential tremor, epilepsy, status epilepticus, and/or nerve agent exposure by administering to the subject a compound as described above and herein (or pharmaceutically composition comprising the compound).

In another embodiment, a method is provided for treating a neurological condition or disorder to a subject in need thereof by administering to the subject a compound as described above and herein (or pharmaceutically composition comprising the compound).

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION

In the following description, certain specific details are set forth in order to provide a thorough understanding of various embodiments. However, one skilled in the art will understand that the present compounds may be made and used without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising," are to be construed in an open, inclusive sense, that is, as "including, but not limited to." In addition, the term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. Headings provided herein are for convenience only and do not interpret the scope or meaning of the claimed embodiments.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise. Thus, for example, reference to "a non-human animal" may refer to one or more non-human animals, or a plurality of such animals, and reference to "a cell" or "the cell" includes reference to one or more cells and equivalents thereof (e.g., plurality of cells) known to those skilled in the art, and so forth. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. It should also be noted that the term "or" is generally employed in its sense including "and/or" unless the content clearly dictates otherwise. The term, "at least one," for example, when referring to at least one compound or to at least one composition, has the same meaning and understanding as the term, "one or more."

Terms not specifically defined herein should be given the meanings that would be given to them by one of skill in the art in light of the disclosure and the context. As used in the specification, however, unless specified to the contrary, the terms have the meaning indicated.

Described herein are compounds useful for treating neurological diseases and/or disorders, which compounds have the following structure (A):

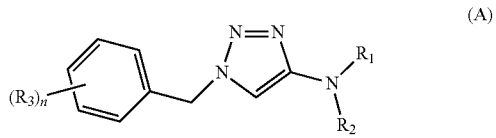

(A)

or a stereoisomer, ester, solvate, or pharmaceutically acceptable salt thereof,
wherein:

$R_1$ is H or $C_{1-4}$alkyl;

$R_2$ is $C_{1-4}$alkyl, —C(═O)O$R_4$, —C(═O)—$C_{1-6}$alkanediyl-NH$_2$, —C(═O)N$R_5R_5$, or —C(═O)$R_6$, wherein said $C_{1-6}$alkanediyl is optionally substituted with a group selected from —NH—C(═NH)NH$_2$, —CO$_2$H, —CO$_2$CH$_3$, —SH, —C(═O)NH$_2$, —NH$_2$, —SCH$_3$, phenyl, —OH, —OC$_{1-4}$alkyl, 4-hydroxy-phenyl, cyclohexyl, imidazolyl, and indolyl;

or $R_1$ and $R_2$ taken together with the N to which they are attached, form a 5-6 member nonaromatic heterocycle wherein the 5-6 member nonaromatic heterocycle may be substituted with 0-3 $R_4$;

$R_3$ at each occurrence is independently Cl, F, $C_{1-4}$alkyl or trifluoromethyl;

$R_4$ at each occurrence is independently $C_{1-4}$alkyl;

$R_5$ at each occurrence is independently H or $C_{1-4}$alkyl;

$R_6$ is $C_{1-4}$alkyl, 5-6 member nonaromatic heterocycle, or 5-6 member heterocycle$C_{1-4}$alkyl wherein 5-6 member heterocycle$C_{1-4}$alkyl is optionally substituted with OH, Cl, F, $C_{1-4}$alkyl, —OC$_{1-4}$alkyl or trifluoromethyl; and n is 0-3.

In one embodiment of structure (A), $R_1$ is $C_{1-4}$alkyl.
In one embodiment of structure (A), $R_1$ is methyl.
In one embodiment of structure (A), $R_1$ is ethyl.
In one embodiment of structure (A), $R_1$ is H.
In one embodiment of structure (A), $R_1$ and $R_2$ are both $C_{1-4}$alkyl.
In one embodiment of structure (A), $R_2$ is $C_{1-4}$alkyl.
In one embodiment of structure (A), $R_2$ is —C(═O)O$R_4$.
In one embodiment of structure (A), $R_2$ is —C(═O)—$C_{1-6}$alkanediyl-NH$_2$. In more specific embodiments, $C_{1-6}$alkanediyl is optionally substituted with a group selected from —NH—C(═NH)NH$_2$, —CO$_2$H, —CO$_2$CH$_3$, —SH, —C(═O)NH$_2$, —NH$_2$, —SCH$_3$, phenyl, —OH, —OC$_{1-4}$alkyl, 4-hydroxy-phenyl, cyclohexyl, imidazolyl, and indolyl. In a certain embodiment, $C_{1-6}$alkanediyl is substituted with —NH—C(═NH)NH$_2$. In a certain embodiment, $C_{1-6}$alkanediyl is substituted with —CO$_2$H. In a certain embodiment, $C_{1-6}$alkanediyl is substituted with —CO$_2$CH$_3$. In a certain embodiment, $C_{1-6}$alkanediyl is substituted with —SH. In a certain embodiment, $C_{1-6}$alkanediyl is substituted with —C(═O)NH$_2$. In a certain embodiment, $C_{1-6}$alkanediyl is substituted with —NH$_2$. In a certain embodiment, $C_{1-6}$alkanediyl is substituted with. —SCH$_3$. In a certain embodiment, $C_{1-6}$alkanediyl is substituted with phenyl. In a certain embodiment, $C_{1-6}$alkanediyl is substituted with —OH. In a certain embodiment, $C_{1-6}$alkanediyl is substituted with —OC$_{1-4}$alkyl. In a certain embodiment, $C_{1-6}$alkanediyl is substituted with 4-hydroxy-phenyl. In a certain embodiment, $C_{1-6}$alkanediyl is substituted with cyclohexyl. In a certain embodiment, $C_{1-6}$alkanediyl is substituted with imidazolyl. In a certain embodiment, $C_{1-6}$alkanediyl is substituted with indolyl.

In one embodiment of structure (A), $R_2$ is —C(═O)N$R_5R_5$.
In one embodiment of structure (A), $R_2$ is —C(═O)$R_6$.
In one embodiment of structure (A), $R_3$ is Cl.
In one embodiment of structure (A), $R_3$ is F.
In one embodiment of structure (A), $R_3$ is $C_{1-4}$alkyl.
In one embodiment of structure (A), $R_3$ is —OC$_{1-4}$alkyl.
In one embodiment of structure (A), $R_3$ is trifluoromethyl
In one embodiment of structure (A), $R_4$ is methyl.
In one embodiment of structure (A), $R_4$ is ethyl.
In one embodiment of structure (A), $R_5$ is H.

In one embodiment of structure (A), $R_5$ is $C_{1-4}$alkyl.
In one embodiment of structure (A), $R_6$ is $C_{1-4}$alkyl.
In one embodiment of structure (A), $R_6$ is a 5-6 member nonaromatic heterocycle.
In one embodiment of structure (A), $R_6$ is a 5-6 member heterocycle$C_{1-4}$alkyl wherein 5-6 member heterocycle$C_{1-4}$alkyl is optionally substituted with OH, Cl, F, $C_{1-4}$alkyl, —OC$_{1-4}$alkyl or trifluoromethyl. In a more specific embodiment, the 5-6 member heterocycle$C_{1-4}$alkyl is substituted with OH. In a particular embodiment, the 5-6 member heterocycle$C_{1-4}$alkyl is substituted with Cl, F, or trifluoromethyl. In a particular embodiment, the 5-6 member heterocycle$C_{1-4}$alkyl is substituted with $C_{1-4}$alkyl or —OC$_{1-4}$alkyl.

In one embodiment of structure (A), n=1.
In one embodiment of structure (A), n=2.
In one embodiment of structure (A), n=3.
In one embodiment of structure (A), $R_1$ and $R_2$ are taken together with the N to which they are attached to form a 5-6 member nonaromatic heterocycle wherein the 5-6 member nonaromatic heterocycle may be substituted with 0-3 $R_4$, as shown in structure (B):

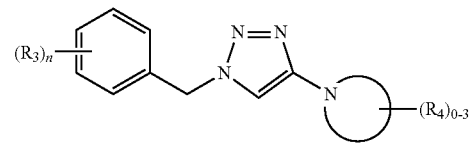

(B)

or a stereoisomer, ester, solvate, and pharmaceutically acceptable salt thereof; wherein $R_3$ and $R_4$ and n are as defined above for structure (A).

In one embodiment of structure (B), the 5-6 member nonaromatic heterocycle further comprises at least one other heteroatom selected from N, S, and O, or further comprises at least one other heteroatom selected from N and O.

In one embodiment of structure (B), n is 1.
In one embodiment of structure (B), n is 1 and $R_3$ is F or Cl.
In one embodiment of structure (B), n is 1 and $R_3$ is F.
In one embodiment of structure (B), n is 1 and $R_3$ is Cl.
In one embodiment of structure (B), n is 1 and $R_3$ is $C_{1-4}$alkyl.
In one embodiment of structure (B), n is 1 and $R_3$ is —OC$_{1-4}$alkyl.
In one embodiment of structure (B), n is 1 and $R_3$ is trifluoromethyl.
In one embodiment of structure (B), n is 2.
In one embodiment of structure (B), n is 2 and $R_3$ at each occurrence is F.
In one embodiment of structure (B), n is 1 and $R_4$ is methyl.
In one embodiment of structure (B), n is 1 and $R_4$ is ethyl.
In one embodiment of structure (B), the 5-6 member nonaromatic heterocycle (i.e., $R_1$ and $R_2$ taken together) is piperazine.
In one embodiment of structure (B), the 5-6 member nonaromatic heterocycle (i.e., $R_1$ and $R_2$ taken together) is morpholine.
In one embodiment of structure (B), the 5-6 member nonaromatic heterocycle (i.e., $R_1$ and $R_2$ taken together) is piperizine.
In one embodiment of structure (B), the 5-6 member nonaromatic heterocycle (i.e., $R_1$ and $R_2$ taken together) is oxazolidine.

In one embodiment of structure (B), the 5-6 member nonaromatic heterocycle (i.e., $R_1$ and $R_2$ taken together) is pyrrolidine.

In certain specific embodiments, the compound is selected from one of the following compounds, including pharmaceutically acceptable salts thereof:

(2 S)-2-amino-N-{1-[(2,6-difluorophenyl)methyl]-1H-1,2,3-triazol-4-yl}-3-phenylpropanamide;
(2R)-2-amino-N-{1-[(2,6-difluorophenyl)methyl]-1H-1,2,3-triazol-4-yl}-3-phenylpropanamide;
(3S)—N-{1-[(2,6-difluorophenyl)methyl]-1H-1,2,3-triazol-4-yl}morpholine-3-carboxamide;
(3R)—N-{1-[(2,6-difluorophenyl)methyl]-1H-1,2,3-triazol-4-yl}morpholine-3-carboxamide;
(2R)-2-amino-N-{1-[(2,6-difluorophenyl)methyl]-1H-1,2,3-triazol-4-yl}-3-methoxypropanamide;
(2R)-2-amino-N-{1-[(2,6-difluorophenyl)methyl]-1H-1,2,3-triazol-4-yl}-3-hydroxypropanamide;
N-[1-(2,6-difluoro-benzyl)-1H-[1,2,3]triazol-4-yl]-3-pyridin-3-yl-propionamide;
3-(3-chlorophenyl)-N-{1-[(4-fluorophenyl)methyl]-1H-1,2,3-triazol-4-yl}propanamide;
(2S)—N-{1-[(2,6-difluorophenyl)methyl]-1H-1,2,3-triazol-4-yl}-2-(2-oxopyrrolidin-1-yl)butanamide;
[1-(2,6-difluoro-benzyl)-1H-[1,2,3]triazol-4-yl]-dimethyl-amine;
[1-benzyl-1H-[1,2,3]triazol-4-yl]-dimethyl-amine;
4-{1-[(2,6-difluorophenyl)methyl]-1H-1,2,3-triazol-4-yl}morpholine;
1-[(2,6-difluorophenyl)methyl]-4-(pyrrolidin-1-yl)-1H-1,2,3-triazole;
1-[(2,6-difluorophenyl)methyl]-N-methyl-1H-1,2,3-triazol-4-amine;
1-[(2,6-difluorophenyl)methyl]-N-ethyl-1H-1,2,3-triazol-4-amine;
2-({1-[(2,6-difluorophenyl)methyl]-1H-1,2,3-triazol-4-yl}amino)ethan-1-ol;
1-{1-[(2,6-difluorophenyl)methyl]-1H-1,2,3-triazol-4-yl}pyrrolidin-2-one;
3-{1-[(2,6-difluorophenyl)methyl]-1H-1,2,3-triazol-4-yl}-1,3-oxazolidin-2-one; or
1-{1-[(2,6-difluorophenyl)methyl]-1H-1,2,3-triazol-4-yl}imidazolidin-2-one.

Certain chemical structures presented herein, particularly in the context of the examples section, may not depict all hydrogen atoms. For example, "—$NH_2$" (i.e., an amine group) may be depicted as "—N" (i.e., absent two hydrogen atoms), a divalent amine ("—NH"—) may be depicted as —"N"—(i.e., absent one hydrogen atom), and an alcohol ("—OH") may be depicted as "—O" (i.e., absent one hydrogen atoms). These and other short-hand notations are well understood be one skilled in this field.

Further, certain chemical groups named herein are preceded by a shorthand notation indicating the total number of carbon atoms that are to be found in the indicated chemical group. For example; $C_1$-$C_4$alkyl describes an alkyl group, as defined below, having a total of 1 to 4 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

As used in the specification and appended claims, unless specified to the contrary, the following terms have the meaning indicated.

"$C_1$-$C_6$alkyl" refers to an alkyl radical as defined below containing one to six carbon atoms. The $C_1$-$C_6$alkyl radical may be optionally substituted as defined below for an alkyl group. "$C_1$-$C_4$alkyl" refers to an alkyl radical as defined below containing one to four carbon atoms. The $C_1$-$C_4$alkyl radical may be optionally substituted as defined below for an alkyl group. "Alkyl" refers to a straight or branched hydrocarbon chain radical consisting solely of carbon and hydrogen atoms, containing no unsaturation, having from one to twelve carbon atoms, one to eight carbon atoms, or one to six carbon atoms, or one to four carbon atoms, and which is attached to the rest of the molecule by a single bond, e.g., methyl, ethyl, n-propyl, 1-methylethyl (iso-propyl), n-butyl, n-pentyl, n-hexyl, and the like. Saturated branched alkyls include isopropyl, sec-butyl, isobutyl, tert-butyl, isopentyl, 3-methylhexyl, 2-methylhexyl, and the like. Representative saturated cyclic alkyls include cyclopropyl, cyclobutyl, cyclopentyl, cyclohexyl, —$CH_2$-cyclopropyl, —$CH_2$-cyclobutyl, —$CH_2$-cyclopentyl, —$CH_2$-cyclohexyl, and the like.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

Unsaturated cyclic alkyls include cyclopentenyl and cyclohexenyl, and the like. Cyclic alkyls, also referred to as "homocyclic rings," include di- and poly-homocyclic rings such as decalin and adamantyl. Unsaturated alkyls contain at least one double or triple bond between adjacent carbon atoms (referred to as an "alkenyl" or "alkynyl," respectively).

"$C_{1-6}$alkanediyl" means a divalent $C_{1-6}$alkyl from which two hydrogen atoms are taken from the same carbon atom or from different carbon atoms, such as —$CH_2$—, —$CH_2CH_2$—, —$CH(CH_3)$— —$CH_2CH_2CH_2$—, —$CH(CH_3)CH_2CH_2$—, —$CHCH(CH_3)_2$—, —$CH_2C(CH_3)_2CH_2$—, and the like.

"Heteroaryl" means an aromatic heterocycle ring of 5- to 10-members and having at least one heteroatom selected from nitrogen, oxygen and sulfur, and wherein the nitrogen and sulfur heteroatoms may be optionally oxidized, and containing at least 1 carbon atom, including both mono- and bicyclic ring systems. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, oxadiazolyl, thiadiazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heterocycle" (also referred to herein as a "heterocycle ring") means a 5- to 7-membered monocyclic, or 7- to 14-membered polycyclic, heterocycle ring which is either saturated (non-aromatic), unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring or a tricyclic (and higher) heterocyclic ring. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperizinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, tetrahydrothiopyranyl, oxopyrrolidinyl, imidazolidinone and the like.

Unless stated otherwise specifically in the specification, each of an alkyl group, an alkenyl group, cyclic alkyl, $C_{1-6}$alkanediyl, and heterocycle may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{40}$, —$OC(O)$—$R^{40}$, —$N(R^{40})_2$, —$C(O)R^{40}$, —$C(O)OR^{40}$, —$C(O)N(R^{40})_2$, —$N(R^{40})C(O)OR^{42}$, —$N(R^{40})C(O)R^{42}$, —$N(R^{40})S(O)_tR^{42}$ (where t is 1 to 2), —$S(O)_tOR^{42}$ (where t is 1 to 2), —$S(O)_pR^{42}$ (where p is 0 to 2), and —$S(O)_tN(R^{40})_2$ (where t is 1 to 2) where each $R^{40}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{42}$ is alkyl, haloalkyl, cycloalkyl, cycloalkylalkyl, aryl, aralkyl, heterocyclyl, heterocyclylalkyl, heteroaryl or heteroarylalkyl.

"Haloalkyl" means an alkyl group having at least one hydrogen atom replaced with a halogen, such as trifluoromethyl and the like.

"Halogen" means fluoro, chloro, bromo or iodo, typically fluoro or chloro.

"Hydroxy" means —OH.

"Alkoxy" means an alkyl moiety attached through an oxygen bridge (i.e., —O-alkyl) and includes groups such as methoxy and ethoxy.

The compounds described herein may generally be utilized as the free acid or free base. Alternatively, the compounds may be used in the form of acid or base addition salts. Acid addition salts of the free amino compounds described herein may be prepared by methods well known in the art, and may be formed from organic and inorganic acids which form non-toxic salts. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of formula (I) is intended to encompass any and all acceptable salt forms.

With regard to stereoisomers, the compounds described herein may have one or more chiral (or asymmetric) centers and may thus give rise to enantiomers, diastereomers, and other stereoisomeric forms that may be defined, in terms of absolute stereochemistry, as (R)- or (S)-. When the compounds described herein contain olefinic double bonds or other centers of geometric asymmetry, and unless specified otherwise, it is intended that the compounds include both E and Z geometric isomers (e.g., cis or trans). Likewise, unless otherwise noted, all possible isomers, as well as their racemic and optically pure forms, and all tautomeric forms are also intended to be included. It is therefore contemplated that various stereoisomers and mixtures thereof include "enantiomers," which refers to two stereoisomers whose molecules are nonsuperimposeable mirror images of one another. Thus, the compounds may occur in any isomeric form, including racemates, racemic mixtures, and as individual enantiomers or diastereomers.

"Prodrug" is meant to indicate a compound that may be converted under physiological conditions or by solvolysis to a biologically active compound described herein. Thus, the term "prodrug" refers to a metabolic precursor of a compound described herein that is pharmaceutically acceptable. A prodrug may be inactive when administered to a subject in need thereof, but is converted in vivo to an active compound as described herein. Prodrugs are typically rapidly transformed in vivo to yield the parent compound described herein, for example, by hydrolysis in blood. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound as described herein in vivo when such prodrug is administered to a mammalian subject. Prodrugs of a compound described herein may be prepared by modifying functional groups present in the compound described herein in such a way that the modifications are cleaved, either in routine manipulation or in vivo, to the parent compound described herein. Prodrugs include compounds described herein wherein a hydroxy, amino or mercapto group is bonded to any group that, when the prodrug of the compound is administered to a mammalian subject, cleaves to form a free hydroxy, free amino or free mercapto group, respectively. Examples of prodrugs include, but are not limited to, ester and amide derivatives of hydroxy, carboxy, mercapto or amino functional groups in the compounds described herein and the like.

The compounds described herein may exist in a continuum of solid states ranging from fully amorphous to fully crystalline. Furthermore, some of the crystalline forms of the compounds of structures (A) or (B) may exist as polymorphs. In addition, some of the compounds of structure (A) or (B) may also form solvates with water or other organic solvents. The term solvate is used herein to describe a molecular complex comprising a compound described herein and one or more pharmaceutically acceptable solvent molecules. Such solvates are similarly included within the scope of this disclosure.

In certain embodiments, the compounds described include all pharmaceutically acceptable isotopically labeled compounds of structures (A) or (B) where on or more atoms are replaced by atoms having the same atomic number but a different atomic mass. Examples include $^2H$ (deuterium) and $^3H$ (tritium) for hydrogen, $^{11}C$, $^{13}C$ and $^{14}C$ for carbon, $^{36}Cl$ for chlorine, $^{18}F$ for fluorine, $^{123}I$ and $^{125}I$ for iodine, $^{13}N$ and $^{15}N$ for nitrogen, and $^{35}S$ for sulfur.

As one of skill in the art would appreciate, any of the aforementioned compounds may incorporate radioactive isotopes. Accordingly, also contemplated is use of isotopically-labeled compounds identical to those described herein, wherein one or more atoms are replaced by an atom having an atomic mass or mass number different from the atomic mass or mass number usually found in nature. Examples of isotopes that can be incorporated into these compounds include isotopes of hydrogen, carbon, nitrogen, oxygen, phosphorous, fluorine and chlorine, such as, but not limited to $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Certain isotopically-labeled compounds, for example those into which radioactive isotopes such as $^3$H and $^{14}$C are incorporated, are also useful in drug or substrate tissue distribution assays. Tritiated hydrogen ($^3$H) and carbon-14 ($^{14}$C) isotopes are particularly preferred for their ease of preparation and detectability. Substitution with heavier isotopes such as deuterium ($^2$H) can provide certain therapeutic advantages resulting from greater metabolic stability, for example increased in vivo half-life or reduced dose requirements and, therefore, may be preferred in some circumstances. Isotopically-labeled compounds can generally be prepared by performing procedures routinely practiced in the art.

Compound Synthesis

The compounds described herein may be prepared by known organic synthesis techniques, including the methods described in more detail in the Examples. In general, the compounds of structures (A) and (B) above may be made by the following reaction schemes, wherein all substituents are as defined above unless indicated otherwise.

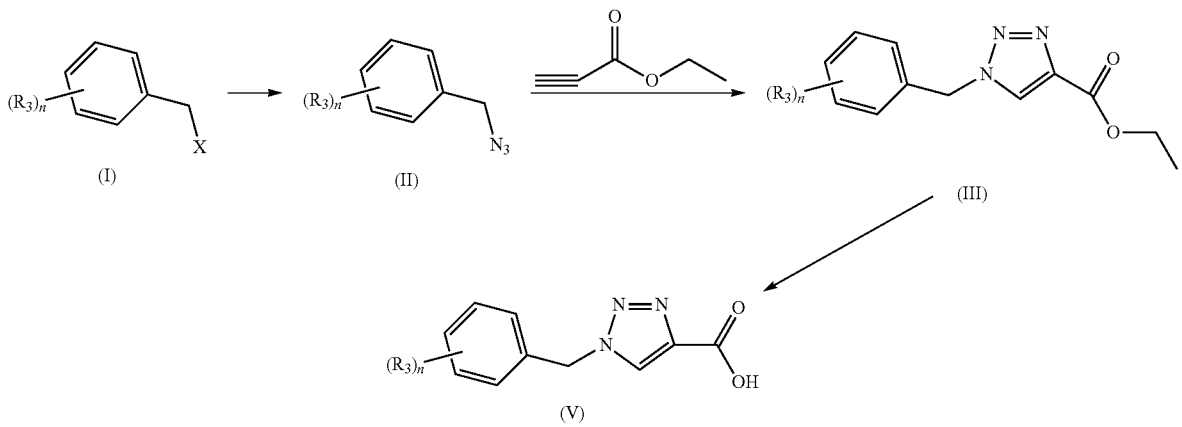

Benzyl halides of the formula (I), where X is a halide, can be reacted with sodium azide in a solvent such as acetonitrile, ethanol or DMF, optionally in the presence of sodium iodide, potassium iodide or n-tetrabutylammonium iodide, at a temperature from room temperature to the boiling point of the solvent to yield azide of formula (II). Azides of formula (II) can be reacted with ethyl propiolate in a solvent such as ethanol at a temperature from room temperature to 90° C. to yield triazoles of formula (III).

Alternatively, triazoles of formula (III) can be treated with a base such as lithium hydroxide or potassium hydroxide, in a solvent mixture such as methanol and H$_2$O or dioxane and H$_2$O, at a temperature from room temperature to the boiling point of the solvent mixture to yield acids of formula (V).

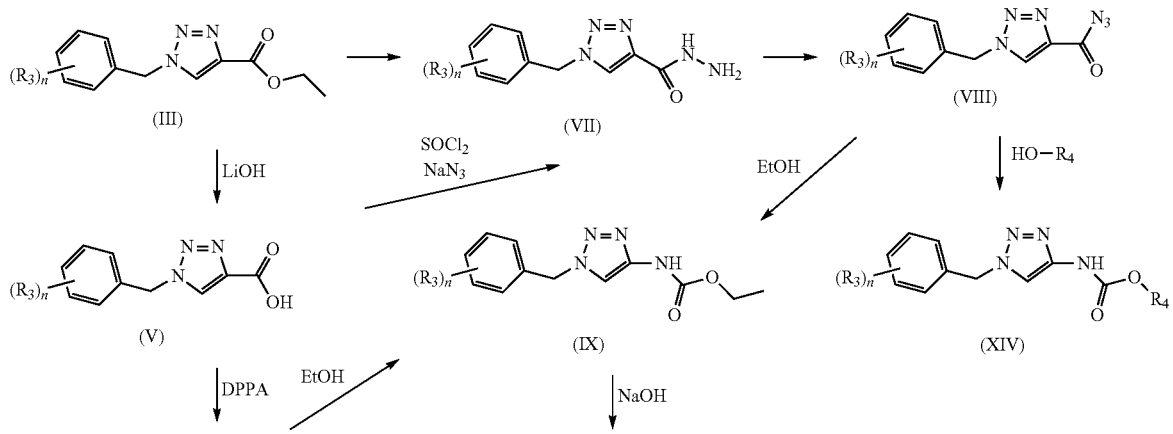

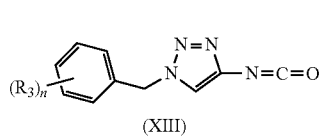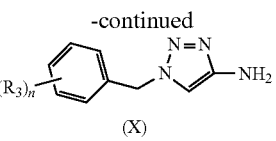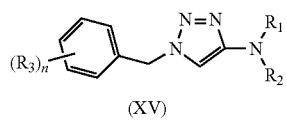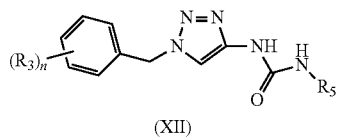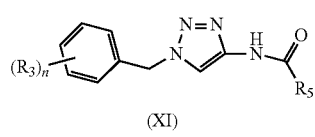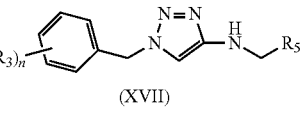

Triazoles of formula (III) can be reacted with hydrazine hydrate in ethanol at a temperature from room temperature to 80° C. to give hydrazides of formula (VII).

Alternatively, triazoles of formula (III) can be treated with a base such as lithium hydroxide or potassium hydroxide, in a solvent mixture such as methanol and $H_2O$, or dioxane and $H_2O$, at a temperature from room temperature to the boiling point of the solvent mixture to yield acids of formula (V).

Hydrazides of formula (VII) can be reacted with sodium nitrite in aqueous hydrochloric acid at a temperature from 0° C. to room temperature to yield azides of formula (VIII). The resulting azides of formula (VIII) can be reacted in ethanol at 85° C. to give compounds of formula (IX).

Alternatively, azides of formula (VIII) can be reacted with alcohols of formula HO—$R_4$ in the presence of a solvent such as tetrahydrofuran, dioxane or DMF, at a temperature from room temperature to the boiling point of the solvent to give carbamates of the formula (XIV).

Amino triazoles of formula (X) are produced by treating compounds of formula (IX) with a base such as sodium hydroxide, lithium hydroxide or potassium hydroxide in ethanol and water at a temperature from room temperature to 85° C.

Amino triazoles of formula (X) can be treated with acids of formula HOOC—$R^5$ using standard coupling conditions using a coupling agent such as HATU in the presence of a base such as N,N-diisopropylethylamine or triethylamine, in a solvent such as dichloromethane or DMF at room temperature to yield compounds of formula (XI). Other suitable coupling conditions include N,N-Dicyclohexylcarbodiimide or 1-Ethyl-3-(3-dimethylaminopropyl)-carbodiimide in the presence of 4-Dimethylaminopyridine and a solvent such as dichloromethane at room temperature. Alternatively, amino triazoles of formula (X) can be treated with acid chlorides of formula ClOC—$R^5$ in the presence of a base such as triethylamine, pyridine or N,N-diisopropylethylamine, in a solvent such as dichloromethane, tetrahydrofuran or dioxane, at a temperature from room temperature to the boiling point of the solvent to give compounds of formula (XI).

Ureas of formula (XII) can be obtained by first reacting amino triazoles of formula (X) with a base such as pyridine, triethylamine or N,N-diisopropylethylamine and triphosgene or phosgene, in a solvent such as dichloromethane at a temperature of 0° C. to room temperature. Subsequently, amines of the formula $H_2N$—$R_5$ are added at room temperature.

Also, acids of formula (V) can be reacted with diphenylphosphoryl azide in the presence of a base such as triethylamine or N,N-diisopropylethylamine, in a solvent such as tert-butanol at a temperature from room temperature to 90° C. to give isocyanates of formula (XIII) which can yield compound (IX) upon treatment with ethanol or compound (XII) upon treatment with an appropriate amine.

Compounds of formula (XVI) where $R_1$ and $R_2$ are taken together to form a heterocycle may be obtained from amines of formula (X) by alkylation with an appropriate bis-electrophile (such as a dihalide, dimesylate, ditosylate, and the like) and an appropriate base such as DIEA or potassium carbonate. Formula (X) and an aldehyde may undergo a reductive amination to yield (XV) where $R_1$=$R_2$. Alternatively, compound (XV) where $R_1$ may be the same or different than $R_2$ may be synthesized via reductive amination of a compound of formula (XVII) and an appropriate aldehyde. A compound of formula (XVII) may be synthesized by boron hydride reduction of compound (XI). In general, the compounds used in the reactions described herein may be made according to organic synthesis techniques known to those skilled in this art, starting from commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art may be identified through various reference books and databases. Suitable reference books and treatise that detail the synthesis of reactants useful in the preparation of compounds of the present disclosure, or provide references to articles that describe the preparation, include for example, "Synthetic Organic Chemistry," John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure," 4th Ed., Wiley-Interscience, New York, 1992. Additional suitable reference books and treatise that detail the synthesis of reactants useful in the preparation of compounds of the present disclosure, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present disclosure is P. H. Stahl & C. G. Wermuth "Handbook of Pharmaceutical Salts," *Verlag Helvetica Chimica Acta*, Zurich, 2002.

Methods for Characterizing and Identifying Compounds

Effectiveness of a compound as a treatment for neurological disorders may be determined by various assay techniques. The Anticonvulsant Screening Program (ASP) of the National Institute of Neurological Diseases and Stroke facilitates the development of new anticonvulsant drugs by providing screening and other services used to evaluate novel candidates in highly predictive and standardized assays. Many of the compounds described herein were tested in one or more assays of the ASP.

The standard models incorporated into anticonvulsant screening include the maximal electroshock test (MES), the subcutaneous Metrazol test (scMET), and evaluations of toxicity (minimal motor impairment, MMI). Additional models include the following: seizures induced by other chemoconvulsants; minimal clonic seizures in mice (6 Hz test); hippocampal-kindled rats; the in vitro spontaneous bursting model of pharmacoresistance in kainate-treated rats; lamotrigine-resistant amygdala-kindled rats; focal seizures in corneal-kindled mice; pilocarpine-induced status epilepticus in rats; and Frings audiogenic seizure susceptible mice.

Maximal Electroshock Test (MES)

The MES is a model for generalized tonic-clonic seizures and provides an indication of a compound's ability to prevent seizure spread when all neuronal circuits in the brain are maximally active. These seizures are highly reproducible and are electrophysiologically consistent with human seizures.

Subcutaneous Metrazol Seizure Threshold Test (scMET)

Excitatory and inhibitory neurotransmission plays a critical role in mediating normal neuronal signaling, and an imbalance between these two pathways can contribute to the onset of seizures, and ultimately epileptogenesis. Chemically disrupting this finely tuned balance can artificially induce a seizure. Subcutaneous injection of the convulsant metrazol produces clonic seizures in laboratory animals. The scMET test detects the ability of a test compound to raise the seizure threshold of an animal and thus protect it from exhibiting a clonic seizure.

Acute Toxicity—Minimal Motor Impairment (MMI)

To assess a compound's undesirable side effects (toxicity), animals are monitored for overt signs of impaired neurological or muscular function. In mice, the rotorod procedure is used to disclose minimal muscular or neurological impairment. When a mouse is placed on a rod that rotates at a speed of 6 rpm, the animal can maintain its equilibrium for long periods of time. The animal is considered to be exhibiting motor impairment if it falls off this rotating rod three times during a 1-min period. In rats, minimal motor deficit is indicated by ataxia, which is manifested by an abnormal, uncoordinated gait. Rats used for evaluating toxicity are examined before the test drug is administered since individual animals may have peculiarities in gait, equilibrium, placing response, etc., which might be attributed erroneously to the test substance. In addition to MMI, animals may exhibit a circular or zigzag gait, abnormal body posture and spread of the legs, tremors, hyperactivity, lack of exploratory behavior, somnolence, stupor, catalepsy, loss of placing response, and changes in muscle tone.

Other Chemoconvulsant Tests

In addition to the intravenous scMET test, other chemoconvulsants can be employed to test for anticonvulsant activity. The $GABA_A$ antagonist, bicuculline, and the $GABA_A$ chloride-channel blocker, picrotoxin, both induce seizures by disrupting normal inhibitory neurotransmission (i.e., weakening synaptic inhibition) through blocking $GABA_A$ receptor function. Both these drugs are used as an acute seizure model for rapid assessment of potential anticonvulsants.

Minimal Clonic Seizure Test

Some clinically useful AEDs are ineffective in the standard MES and scMET tests but still have anticonvulsant activities in vivo. In order to identify potential AEDs with this profile, compounds may be tested in the minimal clonic seizure (6 Hz or 'psychomotor') test. Like the maximal electroshock (MES) test, the minimal clonic seizure test is used to assess a compound's efficacy against electrically-induced seizures but uses a lower frequency (6 Hz) and longer duration of stimulation (3 s). Mice will display seizures characterized by a minimal clonic phase followed by stereotyped, automatistic behaviors described as being similar to the aura of human patients with partial seizures. Animals not displaying this behavior are considered protected. This test may also be conducted at 22 and 44 mA, with 44 mA being more refractory to treatment.

The Hippocampal-Kindled Rat Model

The hippocampal-kindled rat provides an experimental model of focal seizures that become secondarily generalized. This rat model is useful for not only identifying compounds effective against partial seizures, but also allows for the investigation of brain networks that may contribute to seizure spread and generalization from a focus. Moreover, this model provides a temporal framework for assessing drug efficacy in a focal seizure model. Specifically, the refractory period of individual animals is sufficiently short to permit repeated stimulations over a short time span. Second, this kindled rat model can be employed to assess the ability of an investigational compound to block fully kindled seizures evoked by an electrical stimulus. Finally, the hippocampal kindled rat model can also be used to assess the ability of an investigational compound to elevate threshold to focal firing.

The In Vitro Spontaneous Bursting Model of Pharmacoresistance

The medial entorhinal cortex-hippocampal (mEC-HC) slice obtained from kainic acid (KA)-treated animals is an in vitro screen meant to identify compounds that may be effective in pharmacoresistant epilepsy. KA treatment is an accepted animal model of temporal lobe epilepsy (TLE), with an initial insult resulting in status epilepticus, followed by a sustained latent period that subsequently gives way to the development of spontaneous seizures. The mEC-HC slices collected from KA-treated rats exhibit spontaneous electrographic "interictal-like" events that are pharmacoresistant to traditional AEDs. Moreover, the mEC-HC slices obtained from KA-treated rats are hyperexcitable in normal artificial cerebrospinal fluid (ACSF) solution as early as one week following KA-induced SE. This hyperexcitability of slices from KA-treated rats significantly decreases the time it takes for spontaneous burst (SB) discharges to be elicited when compared to the low-$Mg^{2+}$ mEC-HC slice obtained from control rats.

Lamotrigine-(LTG) Resistant Amygdala Kindled Rat Model

The addition of LTG during the development of seizures ultimately impairs the effectiveness of LTG against a fully expressed kindled seizure. Thus, the addition of low doses of LTG during the kindling acquisition phase (through stimulation of an electrode implanted in the amygdala of a rat) produces a model capable of differentiating between traditional anticonvulsants and investigational drugs that are effective in blocking the fully expressed kindled seizure, and may therefore be effective in patients with intractable epilepsy.

Focal Seizures in Corneal-Kindled Mice

In this model, the optic nerve is used to deliver a transcorneal electrical stimulation to the brain in a non-invasive manner. The corneal kindled mouse demonstrates a pharmacological profile consistent with the hippocampal-kindled rat model, and with human partial epilepsy. The nonsurgical nature of the procedure allows for rapid assessment of investigational drugs for this condition, Pilocarpine Induced Status Epilepticus The pilocarpine model is a well characterized model of status epilepticus (SE). This model shares many characteristics with nerve agent induced seizures since the seizures that result in both models are cholinergic mediated. Clinical manifestations following an acute dose of pilocarpine include ataxia, akinesia and facial automatisms. These symptoms quickly progress to full SE which can last up to twelve hours. This activity can be correlated closely with electrographic seizure activity. Rats that survive the acute insult later display spontaneous recurrent seizures and mossy fiber sprouting.

The Frings Audiogenic Seizure-(AGS) Susceptible Mouse Model

Frings AGS-susceptible mice are genetically susceptible to sound-induced reflex seizures. It has a well-validated epilepsy phenotype and is particularly useful as a screening model. Beginning at about 21 days of age, Frings AGS-susceptible mice display prominent seizure activity in response to a high-intensity sound stimulus. They then remain susceptible to sound throughout their life. Their seizure phenotype is characterized by wild running, loss of righting reflex, tonic flexion, and tonic extension in response to high-intensity sound stimulation. In contrast to other seizure models, the Frings AGS-susceptible mouse is non-discriminatory with respect to clinical categories of anticonvulsant drugs. For this reason, this model is used to screen novel investigational compounds, and may also aid in the identification and characterization of compounds effective against inherited forms of epilepsy.

Other tests for efficacy of novel compounds for neurological disorders include the soman-induced seizure model in rats, and the harmaline-induced tremor model in mice.

Soman-Induced Seizures

The organophosphate nerve agent soman induces seizures through irreversible inactivation of the enzyme acetylcholinesterase, resulting in a large increase in cholinergic tone in the brain and peripheral tissues. Rats exposed to soman gas can be used as a model for organophosphate poisoning. Rats exposed to soman rapidly enter a convulsive state, where strong ictal activity can be recorded by EEG. Test compounds are injected intramuscularly or subcutaneously at different times after the onset of seizures. Since human victims in an emergency mass casualty situation are unlikely to gain access to treatment for a long period after initial exposure, those compounds capable of blocking seizure activity when administered at later times after seizure induction will likely be the most efficacious and practical for use.

Harmaline-Induced Tremor

Essential tremor (ET) is the most common movement disorder in humans. While several mechanisms and genetic animal models have been proposed for ET, administration of the β-carboline derivate harmaline to mice is considered the standard model for this disorder. Harmaline causes generalized tremors, with a frequency of 11-14 Hz, the same tremor frequency as ET. Pretreatment with current anti-ET therapeutics such as propranolol (β-blocker) and primidone (antiepileptic) attenuates harmaline-induced tremors in mice.

Compounds described herein as shown in the Examples below (including some chemical intermediates) were generally tested in one or more of the assays shown. A person skilled in the art readily appreciates that in vitro assays and methods and in vivo animal models are performed using the appropriate controls.

The compounds described herein have utility over a wide range of therapeutic applications, and may be used to treat a variety of neurological disorders in humans, both men and women, as well as mammals in general (also referred to herein as a "subject"). For example, the compounds of structures (A) and (B) (as well as the specific compounds disclosed herein) may be used to treat or prevent neurological disorders and diseases, especially essential tremor, epilepsy, status epilepticus, and nerve agent exposure. Such compounds may be used in combination with other anticonvulsant agents, and/or in combination with deep brain stimulation (DBS).

As understood by a person skilled in the medical art, the terms, "treat" and "treatment," refer to medical management of a disease, disorder, or condition of a subject (i.e., patient, individual) (see, e.g., Stedman's Medical Dictionary). In general, an appropriate dose (i.e., effective amount, therapeutic amount) and treatment regimen provide the compound in an amount sufficient to provide therapeutic and/or prophylactic benefit. Therapeutic benefit for subjects to whom the compound(s) described herein are administered, includes, for example, an improved clinical outcome, wherein the object is to prevent or slow or retard (lessen) an undesired physiological change associated with the disease, or to prevent or slow or retard (lessen) the expansion or severity of such disease. As discussed herein, effectiveness of the one or more compounds may include beneficial or desired clinical results that comprise, but are not limited to, abatement, lessening, or alleviation of symptoms that result from or are associated with the disease to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival.

"Treatment" can also mean prolonging survival when compared to expected survival if a subject were not receiving treatment. Subjects in need of treatment include those who already have the disease or disorder as well as subjects prone to have or at risk of developing the disease or disorder, and those in which the disease, condition, or disorder is to be prevented (i.e., decreasing the likelihood of occurrence or recurrence of the disease or disorder).

A subject (i.e., patient, individual) in need of treatment with a compound as described herein may be a human or may be a non-human primate or other animal (i.e., veterinary use) who has developed symptoms of neuronal dysfunction and control including tremor and seizures or who is at risk for developing a neurological disease or disorder, and more specifically symptoms of neuronal dysfunction and control including tremors or seizures. Non-human animals that may be treated include mammals, for example, non-human primates (e.g., monkey, chimpanzee, gorilla, and the like), rodents (e.g., rats, mice, gerbils, hamsters), lagomorphs, swine (e.g., pig, miniature pig), equine, canine, feline, bovine, elephants, bears and other domestic, farm, and zoo animals.

Pharmaceutical Compositions

The present disclosure further provides for pharmaceutical compositions comprising any one of the compounds described herein (a compound of structures (A) and (B), including the specific compounds described herein) and a pharmaceutically acceptable excipient for use in the methods for treating neurological disorders and diseases, especially essential tremor, epilepsy, status epilepticus, and nerve agent exposure. A pharmaceutically acceptable excipient is a physiologically and pharmaceutically suitable non-toxic and inactive material or ingredient that does not interfere with the activity of the active ingredient; an excipient also may be called a carrier.

For the purposes of administration to a subject, the compounds described herein may be formulated as pharmaceutical compositions that comprise a compound and a pharmaceutically acceptable excipient (carrier and/or diluent). The compound is present in the composition in an amount which is effective to treat a particular disorder and preferably with acceptable toxicity to the patient. Appropriate concentrations and dosages can be readily determined by one skilled in the art.

Pharmaceutically acceptable excipients, carriers and diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to the compound, diluents, dispersing and surface active agents, binders, and lubricants. One skilled in this art may further formulate the compound in an appropriate manner, and in accordance with accepted practices. Pharmaceutically acceptable excipients are well known in the pharmaceutical art and described, for example, in Rowe et al., Handbook of Pharmaceutical Excipients: A Comprehensive Guide to Uses, Properties, and Safety, 5$^{th}$ Ed., 2006, and in *Remington: The Science and Practice of Pharmacy* (Gennaro, 21$^{st}$ Ed. Mack Pub. Co., Easton, Pa. (2005)). Examples of pharmaceutically acceptable excipients include sterile saline and phosphate buffered saline at physiological pH. Preservatives, stabilizers, dyes, buffers, and the like may be provided in the pharmaceutical composition. In addition, antioxidants and suspending agents may also be used.

The compounds and pharmaceutical compositions comprising the compounds may be delivered to a subject by any one of several administration methods routinely practiced in the art, including systemic administration. As used herein, systemic administration includes oral and parenteral methods of administration.

For oral administration, suitable pharmaceutical compositions include powders, granules, pills, tablets, lozenges, chews, gels, and capsules as well as liquids, syrups, suspensions, elixirs, and emulsions. The compounds described herein may also be used in fast dissolving, fast disintegrating dosage forms. These compositions may also include antioxidants, flavorants, preservatives, suspending, thickening and emulsifying agents, colorants, flavoring agents and other pharmaceutically acceptable additives. Formulations for oral administration may be formulated to be immediate release or modified release, where modified release includes delayed, sustained, pulsed, controlled, targeted and programmed release.

For parenteral administration, the compounds described herein are administered directly into the blood stream, into muscle, or into an internal organ via an intravenous, intraarterial, intraperitoneal, intramusuclar, subcutaneous or other injection or infusion. Parenteral formulations may be prepared in aqueous injection solutions which may contain, in addition to the compound, buffers, antioxidants, bacteriostats, salts, carbohydrates, and other additives commonly employed in such solutions. Parenteral administrations may be immediate release or modified release (such as an injected or implanted depot).

Compounds and pharmaceutical compositions of same described herein may also be administered topically, (intra) dermally, or transdermally to the skin or mucosa. Typical formulations include gels, hydrogels, lotions, solutions, creams, ointments, dressings, foams, skin patches, wafers, implants and microemulsions. The compounds may also be administered via inhalation or intanasal administration, such as with a dry powder, an aerosol spray or as drops. Additional routes of administration for the compounds described herein include intravaginal and rectal (by means of a suppository, pessary or enema), and ocular, and aural.

The following examples are provided for purposes of illustration, not limitation. In summary, compounds may be assayed by the general methods disclosed in Examples 17-29. The following Examples 1-16 disclose the synthesis of representative compounds of structures (A) and (B).

EXAMPLES

HPLC Methods for Analyzing the Samples (Retention Time, $T_R$, in Minutes)

Method 1: Platform: Agilent 1100 series, equipped with an auto-sampler, an UV detector (220 nm and 254 nm), a MS detector (APCI); HPLC column: Phenomenex Synergi-Max-RP 2.0×50 mm; HPLC gradient: 1.0 mL/min., from 5% acetonitrile in water to 95% acetonitrile in water in 13.5 min., maintaining 95% for 2 min. Both acetonitrile and water have 0.025% TFA.

Method 2: Platform: Dionex, equipped with an auto-sampler, an UV detector (220 nm and 254 nm), a MS detector (APCI); HPLC column: Waters)(Bridge C18, 3.0× 100 mm; HPLC gradient: 1.4 mL/min., from 5% acetonitrile in water to 99% acetonitrile in water in 7.8 min., maintaining 99% for 1.6 min. Both acetonitrile and water have 0.04% $NH_4OH$.

Method 3: Platform: Agilent, equipped with an auto-sampler, an UV detector (220 nm and 254 nm), a MS detector (APCI); HPLC column: Waters XTerraMS C18, 3.0×250 mm; HPLC gradient: 1.0 mL/min., from 10% acetonitrile in water to 90% acetonitrile in water in 46 min. maintaining 90% for 7.0 min. Both acetonitrile and water have 0.025% TFA.

Method 4: Platform: Agilent 1100 series, equipped with an auto-sampler, an UV detector (220 nM and 254 nM), a MS detector (APCI); HPLC column: Phenomenex Synergi: MAX-RP, 2.0×50 mm column; HPLC gradient: 1.0 mL/minute, from 10% acetonitrile in water to 90% acetonitrile in water in 2.5 minutes, maintaining 90% for 1 minute. Both acetonitrile and water have 0.025% TFA.

Example 1

1-[(2,6-Difluorophenyl)methyl]-1H-1,2,3-triazol-4-amine

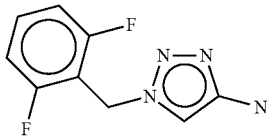

Step 1A: 2,6-Difluorobenzylazide

A mixture of 2,6-difluorobenzyl bromide (4.0 g, 19.3 mmol), sodium iodide (2.9 g, 19.3 mmol) and sodium azide (3.8 g, 57.9 mmol) in acetonitrile (20 mL) was stirred at 70° C. for 12 hours. The solution was diluted with saturated sodium bicarbonate solution and the mixture was extracted with ethyl acetate (3×100 mL). The combined organic extracts were dried ($Na_2SO_4$), and the solvent removed under reduced pressure to yield 2,6-difluorobenzylazide 1a as a light brown oil (65%).

Step 1B: 1-(2,6-Difluoro-benzyl)-1H-[1,2,3]triazole-4-carboxylic acid ethyl ester To a solution of 1a (2.2 g, 13.0 mmol) in ethanol (10.0 mL) was added ethyl propiolate (1.40 g, 14.3 mmol). The reaction mixture was stirred at 80° C. for 5 hours. Upon cooling the product crystallized out. The product crystals were filtered and washed with ethanol. Recrystallization from hot methanol yielded 1-(2,6-difluoro-benzyl)-1H-[1,2, 3]triazole-4-carboxylic acid ethyl ester 1b as off white crystals (45%). LCMS (APCI) m/z 268.0 (MH$^+$). $^1$H NMR (300 MHz, DMSO-d$_6$): δ 8.85 (s, 1H), 7.47-7.57 (m, 1H), 7.14-7.22 (m, 2H), 5.74 (bs, 2H), 4.29 (q, J=7.5 Hz, 2H), 1.28 (t, J=7.5 Hz, 3H).

Step 1C: 1-(2,6-Difluoro-benzyl)-1H-[1,2,3]triazole-4-carboxylic acid

To 1b (2.0 g, 7.5 mmol) stirring in a 1:1 solution of methanol (5.0 mL) and $H_2O$ (5.0 mL) was added lithium hydroxide (0.888 g, 37 mmol). The reaction mixture was heated to 50° C. for 2 hours. Upon cooling, the solution was acidified with aqueous 1 N HCl to a pH of ~3.0. The precipitate was filtered and washed with $H_2O$ (30 mL) and dried in a vacuum oven to yield 1-(2,6-difluoro-benzyl)-1H-[1,2,3]triazole-4-carboxylic acid 1c as an off white solid (85%). LCMS (Method 4) m/z 239.7 [MH$^+$], $t_R$=1.99 min.

Step 1D 1-[(2,6-difluorophenyl)methyl]-1H-1,2,3-triazole-4-carbonyl chloride

To 1c (20 g) was added thionyl chloride (60 mL) and the mixture refluxed for 1 h. The solution was concentrated and dried under vacuum to give the acid chloride 1d as a white solid.

Step 1E 1-[(2,6-difluorophenyl)methyl]-1H-1,2,3-triazole-4-carbonyl azide

Acid chloride 1d was dissolved in acetone (120 mL) and a mixture of sodium azide (8.2 g) in water (100 mL) was added slowly keeping the internal temperature below 10° C. The mixture was left to warm to r.t. overnight. The product was filtered off as a solid washing with water and was dried in a vacuum desiccator over NaOH pellets overnight to give the azide 1e as a white solid (21.6 g).

Step 1F 1-[(2,6-difluorophenyl)methyl]-1H-1,2,3-triazol-4-amine

Azide 1e was refluxed in dry ethanol (100 mL) overnight. NaOH (4 M aqueous, 20 mL) was added carefully and reflux continued overnight. The mixture was cooled to r.t. and HCl (12 N) was slowly added to acidify to pH 1. The ethanol was removed in vacuo and water and DCM were added. The product extracted in to the aqueous layer which was washed with DCM and the organic extracts discarded. The aqueous phase was brought to pH 10 by slow addition of NaOH (12 M, aqueous) and the product precipitated with stirring. After 30 minutes stirring the product was filtered off washing with water several times to give the amine product 1f as an off-white solid (12.3 g). Chromatography on silica gel eluting with ethyl acetate/hexane gave a purer sample for testing. LCMS (Method 4) m/z 211.1 [MH$^+$], $t_R$=1.46 min.

Example 2

1-[(2,6-Difluorophenyl)methyl]-1H-1,2,3-triazol-4-amine

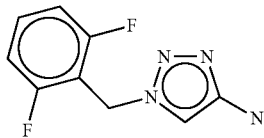

Step 2A: 1-(2,6-Difluoro-benzyl)-1H-[1,2,3]triazole-4-carboxylic acid hydrazide To 1b (1.6 g, 6.0 mmol) was added hydrazine hydrate (0.9 g, 18.0 mmol) and ethanol (5 mL). The reaction mixture was heated in a sealed vessel and heated at 80° C. for 1 hour. The mixture was diluted with H$_2$O (20 mL) and filtered using H$_2$O to rinse the filter cake to yield 1-(2,6-difluoro-benzyl)-1H-[1,2,3]triazole-4-carboxylic acid 2a as an off white solid which was used without additional purification in the next step. LCMS (Method 4) m/z 254.1 [MH$^+$], $t_R$=1.81 min.

Step 2B: 1-(2,6-Difluoro-benzyl)-1H-[1,2,3]triazole-4-carbonyl azide

A mixture of 2a (1.0 g, 3.9 mmol) and sodium nitrite (0.54 g, 7.8 mmol) was stirred in aqueous 2N HCl (5.0 mL) in an ice bath at 0° C. The mixture was allowed to warm to room temperature and stirred for 5 hours. The mixture was diluted with H$_2$O (50 mL) and filtered using cold H$_2$O to rinse the filter cake to yield 1-(2,6-difluoro-benzyl)-1H-[1,2,3]triazole-4-carbonyl azide 1e as a white solid (80% over two steps). LCMS (Method 4) m/z 265.1 [MH$^+$], $t_R$=2.45 min.

Step 2C: [1-(2,6-Difluoro-benzyl)-1H-[1,2,3]triazol-4-yl]-carbamic acid ethyl ester Ethanol (5.0 mL) was added to 1e (1.37 g, 5.2 mmol) and the mixture was stirred at 85° C. for 12 hrs. The mixture was concentrated under vacuum to yield [1-(2,6-difluoro-benzyl)-1H-[1,2,3]triazol-4-yl]-carbamic acid ethyl ester 2c (95% yield). LCMS (Method 4) m/z 283.0 [MH$^+$], $t_R$=2.08 min.

Step 2D: 1-(2,6-Difluoro-benzyl)-1H-[1,2,3]triazol-4-ylamine

To 2c (1.39 g, 4.9 mmol) was added a solution of 1:1 aqueous 2N NaOH/EtOH (5 mL of 2N NaOH, 5 mL of EtOH). The reaction mixture was stirred in a sealed vessel at 85° C. for 1 hour. Upon cooling, the reaction mixture was neutralized to pH 7.5 using aqueous 1N HCl. The solution was diluted with brine and washed with 5% MeOH/DCM (3×50 mL). The combined organic extracts were dried (Na$_2$SO$_4$), and the solvent removed under reduced pressure to yield 1-(2,6-difluoro-benzyl)-1H-[1,2,3]triazol-4-ylamine 1f as an off-white solid (90%). LCMS (Method 1) m/z 211.0 [MH$^+$], $t_R$=2.03 min. $^1$H NMR (300 MHz, CDCl$_3$): δ 7.33 (m, 1H), 6.40 (m, 3H), 5.48 (s, 2H), 3.56 (s, 2H).

Other compounds which were made following this procedure include:

1-(4-fluoro-benzyl)-1H-[1,2,3]triazol-4-ylamine, 2e, LCMS (Method 1) m/z 192.8 [MH$^+$], $t_R$=1.89 min.;

1-(4-trifluoromethyl-benzyl)-1H-[1,2,3]triazol-4-ylamine, 2f, LCMS (Method 4) m/z 243.1 [MH$^+$], $t_R$=1.79 min.;

1-(3-fluoro-benzyl)-1H-[1,2,3]triazol-4-ylamine, 2g, LCMS (Method 4) m/z 193.1 [MH$^+$], $t_R$=1.48 min.; and 1-benzyl-1H-1,2,3-triazol-4-amine, 2h, LCMS (Method 4) m/z 175.1 [MH$^+$], $t_R$=1.40 min.

Example 3

(2S)-2-Amino-N-{1-[(2,6-difluorophenyl)methyl]-1H-1,2,3-triazol-4-yl}-3-phenylpropanamide

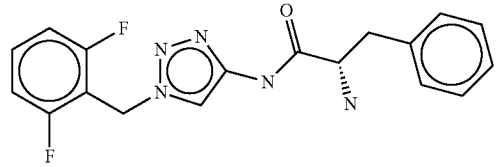

Step 3A: (2S)-2-amino-N-{1-[(2,6-difluorophenyl)methyl]-1H-1,2,3-triazol-4-yl}-3-phenylpropanamide Amino triazole 1f (1.4 g), Boc-L-Phe-OH (1.8 g) and DIEA (1.75 mL) were combined in DCM (10 mL) and DIVIF (10 mL). HATU (3.6 g) was added slowly over 10 minutes with stirring and then was stirred at r.t. overnight. EtOAc and DCM were added and the organic layer was washed with 0.5 M NaOH, 1 M acetic acid, and brine, dried over MgSO$_4$ and concentrated to give a solid. The solid was re-dissolved in hot DCM and ether was added to crystallize product. The resulting solid was filtered, washed with ether and dried by suction to give the Boc-amine product as an off-white solid (2.26 g). The solid was dissolved in DCM (20 mL) and HCl (4M in dioxane, 20 mL) was added and stirred at r.t. for 2 h. Approx. 80% of the solvent was removed in vacuo and ether was added and stirred vigorously to slowly precipitate the product amine as the HCl salt. The solid was filtered off under a stream of N$_2$, washed with ether, dried by suction under a stream of N$_2$ and then in a vacuum desiccator over NaOH pellets overnight. Product amine 3a obtained as a white powder (1.9 g). LCMS (Method 3) m/z 358.2 [MH$^+$], t$_R$=19.65 min. $^1$H NMR (300 MHz, DMSO-d$_6$): δ 8.58 (brs, 2H), 8.20 (s, 1H), 7.43 (m, 1H), 7.16-7.29 (m, 7H), 5.67 (s, 2H), 4.23 (brm, 1H), 3.14 (d, J=6.9 Hz, 2H).

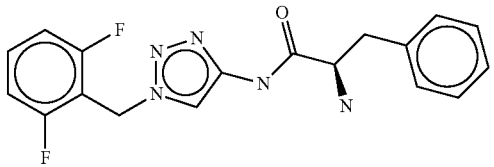

Step 3B: (2R)-2-amino-N-{1-[(2,6-difluorophenyl) methyl]-1H-1,2,3-triazol-4-yl}-3-phenylpropanamide To 1f (0.700 g, 3.3 mmol) in a 1:1 solution of DCM (2.0 mL) and DMF (2.0 mL) was added N-boc-D-phenylalanine (1.3 g, 5.0 mmol) and N,N-diisopropylethylamine (0.645 g, 5.0 mmol). The reaction mixture was stirred at room temperature for 5 minutes then HATU (1.60 g, 4.3 mmol) was added and the mixture was stirred at room temperature for 5 hours. The mixture was diluted with a saturated solution of sodium bicarbonate (100 mL) and washed with DCM (3×100 mL). The combined organic layers were washed with a saturated solution of ammonium chloride (100 mL) then dried (Na$_2$SO$_4$) and the solvent removed under reduced pressure. Purification by silica gel column chromatography eluting with 2% MeOH/DCM gave the Boc-amine product which was then diluted with DCM (3.0 mL) and stirred with 2 N HCl in ether (4.95 mL, 9.9 mmol) at room temperature for 1 hour. The resulting precipitate was filtered, triturated with DCM and filtered again. Drying of the filter cake under reduced pressure yielded amine 3b as a white solid (63%) (HCl salt). LCMS (Method 3) m/z 358.2 [MH$^+$], t$_R$=19.61 min.

Other compounds prepared using this procedure include:

(3S)—N-{1-[(2,6-difluorophenyl)methyl]-1H-1,2,3-triazol-4-yl}morpholine-3-carboxamide, 3c, LCMS (Method 3) m/z 324.2 [MH$^+$], t$_R$=12.52 min.;

(3R)—N-{1-[(2,6-difluorophenyl)methyl]-1H-1,2,3-triazol-4-yl}morpholine-3-carboxamide, 3d, LCMS (Method 3) m/z 324.2 [MH$^+$], t$_R$=12.52 min.;

(2R)-2-amino-N-{1-[(2,6-difluorophenyl)methyl]-1H-1,2,3-triazol-4-yl}-3-methoxypropanamide, 3e, LCMS (Method 3) m/z 312.2 [MH$^+$], t$_R$=9.90 min. $^1$H NMR (300 MHz, DMSO-d$_6$): δ 8.50 (brs, 1H), 8.21 (s, 1H), 7.52 (m, 1H), 7.16-7.22 (m, 2H), 5.68 (s, 2H), 4.18-4.20 (m, 1H), 3.75-3.79 (m, 2H), 3.28 (s, 3H);

(2S)-2-amino-N-(1-benzyl-1H-1,2,3-triazol-4-yl)-3-methoxypropanamide, 3f, LCMS (Method 4) m/z 276.1 [MH$^+$], t$_R$=1.40 min.;

(2S)-2-amino-N-{1-[(3-fluorophenyl)methyl]-1H-1,2,3-triazol-4-yl}-3-methoxypropanamide, 3g, LCMS (Method 4) m/z 294.1 [MH$^+$], t$_R$=1.43 min.;

(2S)-2-amino-N-{1-[(4-fluorophenyl)methyl]-1H-1,2,3-triazol-4-yl}-3-methoxypropanamide, 3h, LCMS (Method 4) m/z 294.1 [MH$^+$], t$_R$=1.43 min.;

(2S)-2-amino-3-methoxy-N-(1-{[4-(trifluoromethyl)phenyl]methyl}-1H-1,2,3-triazol-4-yl)propanamide, 3i, LCMS (Method 4) m/z 344.1 [MH$^+$], t$_R$=1.62 min.;

(2R)-2-amino-N-{1-[(2,6-difluorophenyl)methyl]-1H-1,2,3-triazol-4-yl}-3-hydroxypropanamide, 3j, LCMS (Method 1) m/z 298.1 [MH$^+$], t$_R$=1.66 min.;

(2R)-2-amino-N-{1-[(3-fluorophenyl)methyl]-1H-1,2,3-triazol-4-yl}-3-hydroxypropanamide, 3k, LCMS (Method 4) m/z 280.1 [MH$^+$], t$_R$=1.32 min.;

(2R)-2-amino-N-{1-[(4-fluorophenyl)methyl]-1H-1,2,3-triazol-4-yl}-3-hydroxypropanamide, 3l, LCMS (Method 4) m/z 280.2 [MH$^+$], t$_R$=1.34 min.;

(2R)-2-amino-N-(1-benzyl-1H-1,2,3-triazol-4-yl)-3-hydroxypropanamide, 3m, LCMS (Method 4) m/z 262.1 [MH$^+$], t$_R$=1.24 min.;

(2S)-2-amino-N-{1-[(2,6-difluorophenyl)methyl]-1H-1,2,3-triazol-4-yl}-3-hydroxypropanamide, 3n, LCMS (Method 1) m/z 298.1 [MH$^+$], t$_R$=1.72 min.;

(2S)-2-amino-N-{1-[(4-fluorophenyl)methyl]-1H-1,2,3-triazol-4-yl}-3-hydroxypropanamide, 3o, LCMS (Method 4) m/z 280.1 [MH$^+$], t$_R$=1.33 min.;

(2S)-2-amino-N-(1-benzyl-1H-1,2,3-triazol-4-yl)-3-hydroxypropanamide, 3p, LCMS (Method 4) m/z 262.1 [MH$^+$], t$_R$=1.25 min.; and (2S)-2-amino-3-hydroxy-N-(1-{[4-(trifluoromethyl)phenyl]methyl}-1H-1,2,3-triazol-4-yl)propanamide, 3q, LCMS (Method 4) m/z 330.1 [MH$^+$], t$_R$=1.57 min.

Example 4

2-(1-Aminomethyl-cyclohexyl)-N-[1-(2,6-difluorobenzyl)-1H-[1,2,3]triazol-4-yl]-acetamide

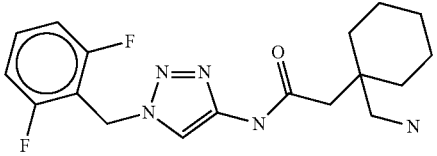

Step 4A: [1-(tert-Butoxycarbonylamino-methyl)-cyclohexyl]-acetic acid

To a solution of gabapentin (2.0 g, 12 mmol) stirring in THF (10.0 mL) and H$_2$O (10.0 mL) was added triethylamine (4.9 mL, 36 mmol) and boc anhydride (5.2 g, 24 mmol). The reaction mixture was stirred at room temperature for 1 hour. The mixture was basified to pH~8 using aqueous 2N NaOH and washed with ethyl acetate (3×100 mL). The aqueous layer was acidified to pH~5 using aqueous 1 N HCL then washed with ethyl acetate (3×100 mL). The combined organic layers from the acidic wash were dried (Na$_2$SO$_4$) and the solvent removed under reduced pressure to yield [1-(tert-butoxycarbonylamino-methyl)-cyclohexyl]-acetic acid 4a as a colorless oil (90%).

Step 4B: 2-(1-Aminomethyl-cyclohexyl)-N-[1-(2,6-difluoro-benzyl)-1H-[1,2,3]triazol-4-yl]-acetamide Compound 4b was prepared according to the procedure of Step 3B using intermediate 4a instead of N-boc-D-phenylalanine. The crude boc-protected product was purified by column chromatography with silica gel, eluting with 2% MeOH/DCM. The boc-protected product was then diluted with DCM (3.0 mL) and stirred with 2 N HCl in ether (4.95 mL, 9.9 mmol) at room temperature for 1 hour. The resulting precipitate was filtered, triturated with DCM and filtered again. Drying of the filter cake under reduced pressure yielded 2-(1-aminomethyl-cyclohexyl)-N-[1-(2,6-difluoro-benzyl)-1H-[1,2,3]triazol-4-yl]-acetamide 4b as a white solid (83%) (HCl salt). LCMS (Method 3) m/z 364.3 [MH$^+$], t$_R$=14.41 min.

(Method 3) m/z 364.2 [MH$^+$], t$_R$=18.07 min. $^1$H NMR (300 MHz, DMSO-d$_6$): δ 8.10 (s, 1H), 7.52 (m, 1H), 7.16-7.23 (m, 7H), 5.63 (s, 2H), 4.59 (m, 1H), 3.58 (m, 1H), 3.2 (m, 1H), 2.23-2.28 (m, 2H), 1.61-1.98 (m, 4H), 0.82 (t, J=7.5 Hz, 3H).

Example 5

N-[1-(2,6-Difluoro-benzyl)-1H-[1,2,3]triazol-4-Yl]-pyridin-4-Yl-PropIonamide

Example 6

3-{1-[(2,6-Difluorophenyl)methyl]-1H-1,2,3-triazol-4-yl}-1-(pyridin-3-ylmethyl)urea

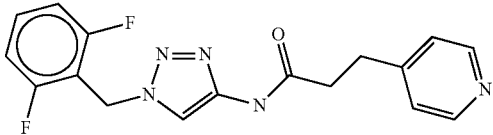

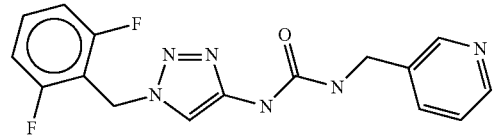

Step 5A: N-[1-(2,6-Difluoro-benzyl)-1H-[1,2,3]triazol-4-yl]-3-pyridin-4-yl-propionamide To 1f (0.700 g, 3.3 mmol) in a 1:1 solution of DCM (2.0 mL) and DMF (2.0 mL) was added 3-(4-pyridinyl)propanoic acid (0.755 g, 5.0 mmol) and N,N-diisopropylethylamine (0.645 g, 5.0 mmol). The reaction mixture was stirred at room temperature for 5 minutes then HATU (1.60 g, 4.3 mmol) was added. The mixture was stirred at room temperature for 5 hours, diluted with a saturated solution of sodium bicarbonate (100 mL) and washed with DCM (3×100 mL). The combined organic layers were washed with a saturated solution of ammonium chloride (100 mL) then dried (Na$_2$SO$_4$) and the solvent removed under reduced pressure to yield a white solid. The solid was triturated with methanol and filtered to yield N-[1-(2,6-difluoro-benzyl)-1H-[1,2,3]triazol-4-yl]-3-pyridin-4-yl-propionamide 5a as a white solid (44%). LCMS (Method 3) m/z 344.2 [MH$^+$], t$_R$=11.31 min. $^1$H NMR (300 MHz, DMSO-d$_6$): δ 10.97 (s, 1H), 8.46 (d, J=6.0 Hz, 2H), 8.11 (s, 1H), 7.52 (m, 1H), 7.16-7.28 (m, 4H), 5.64 (s, 2H), 2.91 (t, J=7.5 Hz, 2H), 2.68 (t, J=7.5 Hz, 2H).

Other compounds made according to this procedure include:

N-[1-(2,6-difluoro-benzyl)-1H-[1,2,3]triazol-4-yl]-3-pyridin-3-yl-propionamide, 5b, LCMS (Method 3) m/z 344.2 [MH$^+$], t$_R$=11.14 min.;

3-(3-chlorophenyl)-N-[1-(4-fluoro-benzyl)-1H-[1,2,3]triazol-4-yl]-propionamide, 5c, LCMS (Method 3) m/z 359.2 [MH$^+$], t$_R$=27.39 min. $^1$H NMR (300 MHz, DMSO-d$_6$): δ 10.90 (s, 1H), 8.18 (s, 1H), 7.18-7.43 (m, 8H), 5.54 (s, 2H), 2.88 (t, J=7.5 Hz, 2H), 2.64 (t, J=7.5 Hz, 2H);

N-{1-[(4-fluorophenyl)methyl]-1H-1,2,3-triazol-4-yl}-3-phenylpropanamide, 5d, LCMS (Method 4) m/z 343.1 [MH$^+$], t$_R$=2.15 min.;

3-(3-chlorophenyl)-N-{1-[(4-fluorophenyl)methyl]-1H-1,2,3-triazol-4-yl}propanamide, 5e, LCMS (Method 4) m/z 359.1 [MH$^+$], t$_R$=2.27 min.;

N-{1-[(4-fluorophenyl)methyl]-1H-1,2,3-triazol-4-yl}-3-phenylpropanamide, 5f, LCMS (Method 4) m/z 325.1 [MH$^+$], t$_R$=2.16 min.;

N-{1-[(4-fluorophenyl)methyl]-1H-1,2,3-triazol-4-yl}-3-(pyridin-3-yl)propanamide, 5g, LCMS (Method 4) m/z 326.1 [MH$^+$], t$_R$=1.49 min.; and (2S)—N-{1-[(2,6-difluorophenyl)methyl]-1H-1,2,3-triazol-4-yl}-2-(2-oxopyrrolidin-1-yl)butanamide, 5h, LCMS Step 6A: 3-{1-[(2,6-difluorophenyl)methyl]-1H-1,2,3-triazol-4-yl}-1-(pyridin-3-ylmethyl)urea To 1f (0.030 g, 0.14 mmol) stirring in DCM (0.5 mL) was added pyridine (0.055 g, 0.70 mmol) and triphosgene (0.038 g, 0.13 mmol). The reaction mixture was stirred in a 0° C. ice bath for 30 minutes then 3-(aminomethyl)pyridine (0.075 g, 0.7 mmol) was added. The reaction mixture was stirred at room temperature overnight. Purification by preparative HPLC-MS yielded 1-[1-(2,6-Difluoro-benzyl)-1H-[1,2,3]triazol-4-yl]-3-pyridin-3-ylmethyl-urea 6a as a TFA salt (35%). LCMS (Method 5) m/z 345.1 [MH$^+$], t$_R$=3.54 min.

Other compounds made according to the above procedure include:

3-{1-[(2,6-difluorophenyl)methyl]-1H-1,2,3-triazol-4-yl}-1-(pyridin-2-ylmethyl)urea, 6b, LCMS (Method 2) m/z 345.4 [MH$^+$], t$_R$=2.72 min.; and 3-{1-[(2,6-difluorophenyl)methyl]-1H-1,2,3-triazol-4-yl}-1-(pyridin-4-ylmethyl)urea, 6c, LCMS (Method 5) m/z 345.1 [MH$^+$], t$_R$=2.65 min.

Example 7

[1-(2,6-Difluoro-benzyl)-1H-[1,2,3]triazol-4-yl]-carbamic acid benzyl ester

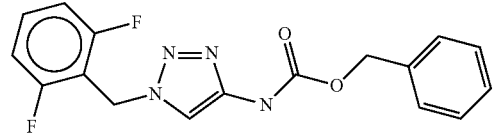

Step 7A: [1-(2,6-Difluoro-benzyl)-1H-[1,2,3]triazol-4-yl]-carbamic acid benzyl ester To azide 1e (0.40 g, 1.5 mmol) in DMF (3.0 mL) was added benzyl alcohol (0.486 g, 4.5 mmol). The reaction mixture was heated to 80° C. for 24 hours. Upon cooling, the mixture was diluted with brine and washed with DCM (3×100 mL). The combined organic layers were dried (Na$_2$SO$_4$) and the solvent removed under reduced pressure. Purification by column chromatography with silica gel, eluting with 2% MeOH/DCM gave [1-(2,6-difluoro-benzyl)-1H-[1,2,3]triazol-4-yl]-carbamic acid benzyl ester 7a (87%). LCMS (Method 2) m/z 345.2 [MH⁺], $t_R$=5.36 min. ¹H NMR (300 MHz, CDCl₃): δ 7.92 (s, 1H), 7.15-7.57 (m, 8H), 5.63 (s, 2H), 5.14 (s, 2H).

Example 8

[1-(2,6-Difluoro-benzyl)-1H-[1,2,3]triazol-4-yl]-dimethyl-amine

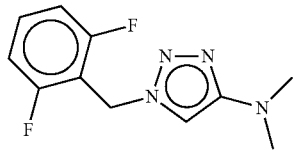

Step 8A: [1-(2,6-Difluoro-benzyl)-1H-[1,2,3]triazol-4-yl]-dimethyl-amine

To 1f (1.5 g, 7.1 mmol) was added acetic acid (20 mL), paraformaldehyde (2.1 g, 71 mmol) and sodium cyanoborohydride (1.4 g, 21.3 mmol). The reaction mixture was stirred at room temperature for 12 hours. The reaction was basified with aqueous 1 N NaOH while stirring on ice and was washed with DCM (3×200 mL). The combined organic layers were dried (Na₂SO₄), and the solvent removed under reduced pressure. Purification by column chromatography with silica gel, eluting with 5% MeOH/DCM+0.5% TEA gave [1-(2,6-difluoro-benzyl)-1H-[1,2,3]triazol-4-yl]-dimethyl-amine 8a (35%). LCMS (Method 3) m/z 239.2 [MH⁺], $t_R$=15.82 min. ¹H NMR (300 MHz, CDCl₃): δ 8.03 (s, 1H), 7.42 (m, 1H), 6.96-7.04 (m, 2H), 5.64 (s, 2H), 3.21 (s, 6H).

Other compounds prepared using the above procedure include:

[1-(4-fluoro-benzyl)-1H-[1,2,3]triazol-4-yl]-dimethyl-amine, 8b, LCMS (Method 4) m/z 221.1 [MH⁺], $t_R$=1.82 min.;

[1-(3-fluoro-benzyl)-1H-[1,2,3]triazol-4-yl]-dimethyl-amine, 8c, LCMS (Method 4) m/z 221.1 [MH⁺], $t_R$=1.84 min.;

[1-(4-trifluoromethyl-benzyl)-1H-[1,2,3]triazol-4-yl]-dimethyl-amine, 8d, LCMS (Method 4) m/z 271.1 [MH⁺], $t_R$=2.06 min.;

[1-benzyl-1H-[1,2,3]triazol-4-yl]-dimethyl-amine, 8e, LCMS (Method 4) m/z 203.1 [MH⁺], $t_R$=1.77 min.; and 1-[(2,6-difluorophenyl)methyl]-N,N-diethyl-1H-1,2,3-triazol-4-amine, 8f, LCMS (Method 1) m/z 267.0 [MH⁺], $t_R$=5.27 min. ¹H NMR (HCl salt; 300 MHz, CDCl₃): δ 8.29 (brs, 1H), 7.41 (m, 1H), 7.00 (t, 2H), 5.68 (s, 2H), 3.60 (m, 4H), 1.28 (m, 6H).

Example 9

1-[1-(2,6-Difluoro-benzyl)-1H-[1,2,3]triazol-4-yl]-4-methyl-piperazine

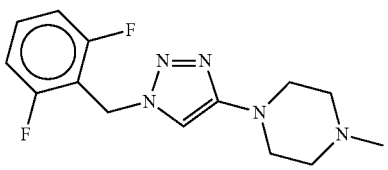

Step 9A: 1-[1-(2,6-Difluoro-benzyl)-1H-[1,2,3]triazol-4-yl]-4-methyl-piperazine

To 1f (0.030 g, 0.14 mmol) in a 2:1 solution of toluene (0.400 mL) and DMF (0.200 mL) was added mechlorethamine hydrochloride (0.025 g, 0.13 mmol) and N,N-diisopropylethylamine (0.072 mg, 0.56 mmol). The reaction mixture was stirred at 100° C. for 12 hours. Purification by preparative HPLC-MS yielded 1-[1-(2,6-difluoro-benzyl)-1H-[1,2,3]triazol-4-yl]-4-methyl-piperazine 9a as a TFA salt (30%). LCMS (Method 2) m/z 294.3 [MH⁺], $t_R$=2.65 min.

Example 10

4-{1-[(2,6-Difluorophenyl)methyl]-1H-1,2,3-triazol-4-yl}morpholine

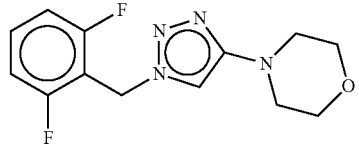

Step 10A: 4-{1-[(2,6-difluorophenyl)methyl]-1H-1,2,3-triazol-4-yl}morpholine

To a solution of amine 1f (1.0 g) in acetonitrile (20 mL) was added potassium carbonate (2 g, powdered) and 1-bromo-2-(2-bromoethoxy)ethane (1.3 g) and the reaction heated in a microwave at 120° C. for 1.5 h. Additional 1-bromo-2-(2-bromoethoxy)ethane (1.3 g) was added and heated at 120° C. for a further 1.5 h. The mixture was filtered washing with DCM and the filtrate was concentrated and purified by chromatography on silica gel eluting with ethyl acetate/hexane and then further purified by chromatography on silica gel eluting with acetone/hexane to give 4-{1-[(2,6-difluorophenyl)methyl]-1H-1,2,3-triazol-4-yl}morpholine 10a (495 mg) as an off-white solid. LCMS (Method 1) m/z 280.9 [MH⁺], $t_R$=4.14 min. ¹H NMR (300 MHz, CDCl₃): δ 7.36 (m, 1H), 6.96 (t, 2H), 6.79 (s, 1H), 5.53 (s, 2H), 3.82 (m, 4H), 3.16 (m, 4H).

Other compounds prepared using the above procedure include:

4-{1-[(4-fluorophenyl)methyl]-1H-1,2,3-triazol-4-yl}morpholine, 10b,

LCMS (Method 2) m/z 263.1 [MH⁺], $t_R$=1.79 min.;

4-{1-[(3-fluorophenyl)methyl]-1H-1,2,3-triazol-4-yl}morpholine, 10c,

LCMS (Method 2) m/z 263.1 [MH⁺], $t_R$=1.80 min.;

4-{1-[(4-trifluoromethylphenyl)methyl]-1H-1,2,3-triazol-4-yl}morpholine,

10d, LCMS (Method 2) m/z 313.1 [MH⁺], $t_R$=2.02 min.;

4-(1-benzyl-1H-1,2,3-triazol-4-yl)morpholine, 10e, LCMS (Method 2) m/z 245.2 [MH⁺], $t_R$=1.74 min.; and 1-[(2,6-difluorophenyl)methyl]-4-(pyrrolidin-1-yl)-1H-1,2,3-triazole, 10f, LCMS (Method 1) m/z 265.0 [MH⁺], $t_R$=5.11 min. ¹H NMR (300 MHz, CDCl₃): δ 7.35 (m, 1H), 6.96 (t, 2H), 6.71 (s, 1H), 5.51 (s, 2H), 3.27 (m, 4H), 1.92 (m, 4H).

Example 11

1-[(2,6-Difluorophenyl)methyl]-N-methyl-1H-1,2,3-triazol-4-amine

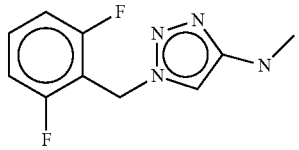

Step 11A: N-{1-[(2,6-difluorophenyl)methyl]-1H-1,2,3-triazol-4-yl}formamide To a solution of amine 1f (1.3 g) in acetonitrile (12 mL) was added ammonium formate (5 g) and the reaction was heated in a sealed vessel at 130° C. overnight. Additional ammonium formate (2 g) was added and heating continued at 130° C. for 3 h. After cooling to r.t. and concentration, water was added and the solid filtered off washing with water to give formamide 11a (1.22 g) as a white solid. LCMS (Method 4) m/z 310.9 [MH$^+$], $t_R$=2.24 min.

Step 11B: 1-[(2,6-difluorophenyl)methyl]-N-methyl-1H-1,2,3-triazol-4-amine

To a solution of formamide 11a (1.22 g) in THF (40 mL) was added a solution of borane (18.5 mL, 1 M in THF) and the mixture was stirred at r.t. overnight. Methanol (20 mL) was added carefully followed by HCl (10 mL, 1 N aqueous) and stirred at r.t. overnight. The reaction was concentrated, diluted with DCM and washed with NaOH (50 mL, 2 N aqueous) and water. The organic phase was dried over sodium sulfate, concentrated and purified by silica gel chromatography eluting with ethyl acetate/hexanes to give 1-[(2,6-difluorophenyl)methyl]-N-methyl-1H-1,2,3-triazol-4-amine 11b (0.67 g) as a white solid. LCMS (Method 4) m/z 225.0 [MH$^+$], $t_R$=2.03 min.

Example 12

N-{1-[(2,6-Difluorophenyl)methyl]-1H-1,2,3-triazol-4-yl}acetamide

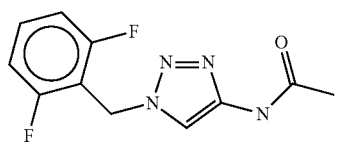

Step 12A: N-{1-[(2,6-difluorophenyl)methyl]-1H-1,2,3-triazol-4-yl}acetamide To a slurry of amine 1f (1.0 g) in DCM (40 mL) was added triethylamine (0.86 mL) followed by acetyl chloride (0.37 mL) slowly with cooling in an ice bath. Warming to r.t. and concentration gave the crude amide 12a. LCMS (Method 4) m/z 252.9 [MH$^+$], $t_R$=1.95 min.

Other compounds prepared using the above procedure include:

N-{1-[(3-fluorophenyl)methyl]-1H-1,2,3-triazol-4-yl}acetamide, 12b, LCMS (Method 4) m/z 235.1 [MH$^+$], $t_R$=1.70 min.;

N-{1-[(4-fluorophenyl)methyl]-1H-1,2,3-triazol-4-yl}acetamide, 12c, LCMS (Method 4) m/z 235.1 [MH$^+$], $t_R$=1.70 min.;

N-(1-{[4-(trifluoromethyl)phenyl]methyl}-1H-1,2,3-triazol-4-yl)acetamide, 12d, LCMS (Method 4) m/z 285.1 [MH$^+$], $t_R$=1.92 min.;

N-(1-benzyl-1H-1,2,3-triazol-4-yl)propanamide, 12e, LCMS (Method 4) m/z 231.1 [MH$^+$], $t_R$=1.76 min.;

N-{1-[(3-fluorophenyl)methyl]-1H-1,2,3-triazol-4-yl}propanamide, 12f, LCMS (Method 4) m/z 249.1 [MH$^+$], $t_R$=1.81 min.; and N-{1-[(4-fluorophenyl)methyl]-1H-1,2,3-triazol-4-yl}propanamide, 12g, LCMS (Method 4) m/z 249.1 [MH$^+$], $t_R$=1.81 min.

Step 12B: 1-[(2,6-difluorophenyl)methyl]-N-ethyl-1H-1,2,3-triazol-4-amine

To a slurry of the crude amide 12a in THF (20 mL) was added Lithium Aluminum Hydride (1 M in THF, 8.3 mL) and the mixture was stirred at r.t for 3 days. The reaction was quenched by addition of Rochelle's salt (saturated aqueous) and extracted with ethyl acetate (2×100 mL). The organic phase was extracted with HCl (1 N, aqueous) and the organic discarded. The aqueous phase was basified with NaOH (2 N, aqueous) to pH 8 and the product extracted into ethyl acetate (2×30 mL). The organic was washed with brine, dried over magnesium sulfate and concentrated to give 1-[(2,6-difluorophenyl)methyl]-N-ethyl-1H-1,2,3-triazol-4-amine_12h as a white solid. LCMS (Method 4) m/z 211.0 [MH$^+$], $t_R$=2.11 min.

Example 13

2-({1-[(2,6-Difluorophenyl)methyl]-1H-1,2,3-triazol-4-yl}amino)ethan-1-ol

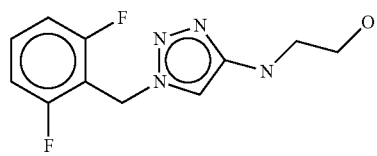

Step 13A: ({1-[(2,6-difluorophenyl)methyl]-1H-1,2,3-triazol-4-yl}carbamoyl)methyl acetate To a slurry of amine 1f (1.3 g) in DCM (40 mL) was added triethylamine (1.1 mL) followed by acetoxyacetyl chloride (0.73 mL) slowly at r.t. and stirred for 1 h. After washing with saturated sodium bicarbonate and water the organic was dried over sodium sulfate and concentrated to give ({1-[(2,6-difluorophenyl)methyl]-1H-1,2,3-triazol-4-yl}carbamoyl)methyl acetate 13a (1.9 g) as a white solid. LCMS (Method 4) m/z 310.9 [MH⁺], $t_R$=2.24 min.

Step 13B: 2-({1-[(2,6-difluorophenyl)methyl]-1H-1,2,3-triazol-4-yl}amino)ethan-1-ol To a slurry of amide 13a (1.9 g) in THF (40 mL) was added a solution of borane (18.5 mL, 1 M in THF) and refluxed for 8 h. Methanol (20 mL) was added carefully followed by HCl (6 N, aqueous) and the mix was stirred at 60° C. overnight. After cooling the mixture was concentrated, diluted with DCM and washed with NaOH (50 mL, 2 N aqueous) and water. The organic phase was dried over sodium sulfate, concentrated and purified by silica gel chromatography eluting with ethyl acetate/hexanes to give 2-({1-[(2,6-difluorophenyl)methyl]-1H-1,2,3-triazol-4-yl}amino)ethan-1-ol 13b (0.91 g) as a white solid. LCMS (Method 4) m/z 254.9 [MH⁺], $t_R$=1.92 min.

Example 14

1-{1-[(2,6-Difluorophenyl)methyl]-1H-1,2,3-triazol-4-yl}pyrrolidin-2-one

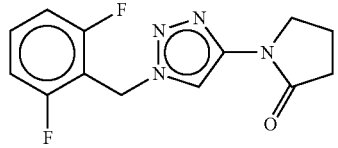

Step 14A: 1-{1-[(2,6-difluorophenyl)methyl]-1H-1,2,3-triazol-4-yl}pyrrolidin-2-one To a solution of amine 1f (400 mg) in DCM (8 mL) was added DIEA (0.41 mL) followed by 4-chlorobutanoyl chloride (0.23 mL) and the mixture was stirred at r.t. overnight. The reaction mixture was dried down and DMF (2 mL) was added and the reaction dried down again and then re-dissolved in DMF. NaH (169 mg, 60% in oil) was added with stirring and the reaction heated at 60° C. overnight. Extra NaH (60 mg, 60% in oil) was added and heated at 60° C. overnight again to complete the reaction. DCM and ammonium chloride were added and the organic was separated and dried over magnesium sulfate and concentrated. Chromatography on silica gel eluting with ethyl acetate/hexane gave the lactam 1-{1-[(2,6-difluorophenyl)methyl]-1H-1,2,3-triazol-4-yl}pyrrolidin-2-one 14a (230 mg) as a white solid. LCMS (Method 1) m/z 279.1 [MH⁺], $t_R$=4.50 min. ¹H NMR (300 MHz, CDCl₃): δ 8.13 (s, 1H), 7.35 (m, 1H), 6.96 (t, J=7.0 Hz, 2H), 5.60 (s, 2H), 4.07 (t, J=7.8 Hz, 2H), 2.55 (t, 2H), 2.21 (app qn, J=7.4 Hz, 2H).

Example 15

3-{1-[(2,6-Difluorophenyl)methyl]-1H-1,2,3-triazol-4-yl}-1,3-oxazolidin-2-one

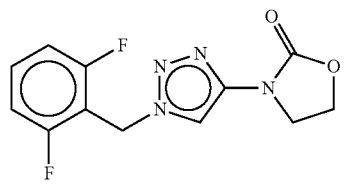

Example 15A: 3-{1-[(2,6-difluorophenyl)methyl]-1H-1,2,3-triazol-4-yl}-1,3-oxazolidin-2-one To a solution of crude amine 13b (1.3 g, without purification) in DCM (100 mL) was added triethylamine (1.8 mL) followed by triphosgene (0.65 g). The mixture was stirred at r.t. overnight. Additional triphosgene (0.06 g) was added and stirred overnight. The reaction was washed with water, saturated sodium bicarbonate, dried over sodium sulfate and concentrated. Chromatography on silica gel eluting with ethyl acetate/hexane gave carbamate 3-{1-[(2,6-difluorophenyl)methyl]-1H-1,2,3-triazol-4-yl}-1,3-oxazolidin-2-one 15a (0.65 g) as a white solid. LCMS (Method 1) m/z 281.1 [MH⁺], $t_R$=4.36 min. ¹H NMR (300 MHz, CDCl₃): δ 7.91 (s, 1H), 7.38 (m, 1H), 6.97 (t, 1H), 5.62 (s, 2H), 4.56 (t, 2H), 4.23 (t, 2H).

Example 16

1-{1-[(2,6-Difluorophenyl)methyl]-1H-1,2,3-triazol-4-yl}imidazolidin-2-one

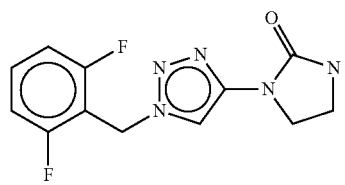

Step 16A: 1-{1-[(2,6-difluorophenyl)methyl]-1H-1,2,3-triazol-4-yl}imidazolidin-2-one To a solution of amine 1f (5.0 g, 23.8 mmol) and Boc-glycine (5.0 g, 28.6 mmol) in DCM (40 mL) and DMF (40 mL) was added DIEA (6.2 mL) followed by HATU (12.7 g) and the mixture was stirred at r.t. for 3 days. The reaction was concentrated to remove DCM and excess water was then added. The solid was filtered off washing with water and dried under vacuum to give the amide as an off-white solid (8.6 g). The amide product was dissolved in DCM (40 mL) and HCl (4 M in dioxane, 40 mL) was added and stirred at r.t. for 1 h. NaOH (4 M aqueous) was added carefully to basify and additional DCM added. The organic layer was dried over magnesium sulfate and concentrated to give the crude amine. The amine was dissolved in THF (20 mL) and borane (1 M in THF, 72 mL) was added and the solution was heated at 60° C. for 16 h. At 60° C. with rapid stirring MeOH (20 mL) was added carefully followed by HCl (4 M in dioxane, 35 mL) carefully and then refluxed for 1.5 h. The reaction was cooled, concentrated (approx. 80% solvent removed) and ether was added to precipitate the diamine as the HCl salt. The product was filtered under a stream of nitrogen washing with ether and dried by suction under a nitrogen stream to give a white solid (6.95 g, assumed di-HCl salt). The diamine (6.95 g) was dissolved in DCM (200 mL) containing excess DIEA (15 mL) and triphosgene (2.12 g in 50 mL DCM) was added slowly at r.t. After 1 h the reaction mixture was washed with HCl (1 M aqueous, 2×50 mL), NaOH (2 M aqueous, 50 mL), water and brine, and washed dried over magnesium sulfate and concentrated to give a white solid. The solid was re-dissolved in DCM (minimum amount to dissolve) and precipitated by addition of ether. The solid was filtered off washing with ether to give 1-{1-[(2,6-difluorophenyl)methyl]-1H-1,2,3-triazol-4-yl}imidazolidin-2-one 16a (3.45 g) as a white solid. LCMS (Method 1) m/z 280.0 [MH$^+$], $t_R$=3.42 min. $^1$H NMR (300 MHz, CDCl$_3$): δ 7.95 (s, 1H), 7.50 (m, 1H), 7.18 (t, 2H), 7.07 (s, 1H), 5.62 (s, 2H), 3.87 (t, 2H), 3.43 (t, 2H).

Example 17

Maximal Electroshock Test

All animal model experiments described herein were performed in male rodents (albino Carworth Farms No. 1 (CF-1) mice, or albino Sprague-Dawley rats). Housing, handling, and feeding were in accordance with recommendations contained in the 'Guide for the Care and Use of Laboratory Animals'. Many of the following experiments were performed by the Anticonvulsant Screening Program (ASP) of the National Institute of Neurological Diseases and Stroke. The Department of Health and Human Services recently expanded the scope of the ASP to include counter measures for exposure to nerve agents.

In vivo antiseizure activity was measured by the maximal electroshock (MES) test. Adult male CF-1 albino mice (18-25 g) or Sprague-Dawley rats (100-150 g) were utilized for these experiments. An alternating current of 60 Hz (50 mA in mice, 150 mA in rats) was delivered for 0.2 sec by corneal electrodes which had been primed with an electrolyte solution containing 0.5% tetracaine HCl anesthetic. The endpoint for protection from MES-induced seizures is the abolition of the hindlimb tonic extensor component of the seizure. Mice were tested at various time intervals following doses of test compound given by intraperitoneal administration using a volume of 0.01 ml/g in mice, and rats were screened with 0.04 ml/g (both i.p. and p.o.). The compounds listed in Table 1 were shown to be active at the single dose stated, or with an $ED_{50}$ if multiple doses were tested (data are for mice administered i.p. and for rat administered p.o., mpk=mg/kg).

TABLE 1

| Compound | Mouse (IP) | Rat (PO) |
| --- | --- | --- |
| 3a | MES active at 100 mpk | MES $ED_{50}$ 25 mpk |
| 3b | MES $ED_{50}$ 56 mpk | MES $ED_{50}$ 24 mpk |
| 3c | MES $ED_{50}$ 20 mpk | MES active at 15 mpk |
| 3d | MES $ED_{50}$ 73 mpk | MES $ED_{50}$ 24 mpk |
| 3e | MES $ED_{50}$ 40 mpk | MES active at 30 mpk |
| 3j | MES active at 100 mpk | MES $ED_{50}$ 29 mpk |
| 5b | MES active at 300 mpk | — |
| 5e | MES active at 100 mpk | — |
| 5h | MES active at 300 mpk | — |

TABLE 1-continued

| Compound | Mouse (IP) | Rat (PO) |
| --- | --- | --- |
| 8a | MES $ED_{50}$ 27 mpk | MES $ED_{50}$ 9 mpk |
| 8e | MES active at 100 mpk | — |
| 10a | MES $ED_{50}$ 31 mpk | MES $ED_{50}$ 44 mpk |
| 10f | MES $ED_{50}$ 73mpk | MES active at 30 mpk |
| 11b | MES active at 100 mpk | MES active at 30 mpk |
| 12h | MES active at 100 mpk | MES active at 30 mpk |
| 13b | MES active at 30 mpk | MES active at 30 mpk |
| 14a | MES active at 100 mpk | MES $ED_{50}$ 28 mpk |
| 16a | MES $ED_{50}$ 8 mpk | MES $ED_{50}$ 7 mpk |

Example 18

Subcutaneous Metrazol Seizure Threshold Test

Animals are pretreated with various doses of test compound as for the MES tests. The dose of metrazol which induced convulsions in 97% of control animals (85 mg/kg in mice) is injected into a loose fold of skin in the midline of the neck. To minimize stress, animals are placed in isolation cages and observed for the next 30 min for the presence or absence of a seizure. Continuous observation allows the time to peak effect (TPE) for each drug to be determined. An episode of clonic spasms, lasting approximately 3-5 s, of the fore- and/or hindlimbs, jaws or vibrissae is taken as the endpoint. Animals that do not meet this criterion are considered protected.

Example 19

Acute Toxicity—Minimal Motor Impariment

Animals are monitored for overt signs of impaired neurological or muscular function. In mice, the rotorod test is used. An untreated mouse, when placed on a rod that rotates at a speed of 6 rpm, can maintain its equilibrium for long periods of time. The test compound are considered toxic if the mouse falls off this rotating rod three times during a 1-min period. In rats, minimal motor deficit was indicated by ataxia (manifested by an abnormal, uncoordinated gait). In addition to minimal motor impairment, the animals are observed for other abnormal signs including abnormal body posture, tremors, hyperactivity, lack of exploratory behavior, or somnolence. Dose response curves for toxicity can be produced in order for a dose toxic in 50% of animals ($TD_{50}$) to be determined.

Example 20

Chemoconvulsant-Induced Seizures

The test compound is given at or below the $TD_{50}$ dose and tested at the s.c. metrazol time of peak effect (TPE). This test measures the ability of the test substance to prevent a clonic seizure produced by the s.c. injection of either bicuculline (2.7 mg/kg) or picrotoxin (2.5 mg/kg). Following the administration of bicuculline, CF-1 mice are placed in isolation cages and observed for 30 min for the presence or absence of a seizure; those receiving picrotoxin are observed for 45 min because of the slower absorption of this convulsant. Seizures typically consisted of an episode of clonic spasms of the fore- and hind limbs, jaws and vibrissae. Bicuculline-induced clonic seizures are generally followed by tonic extension of the hind limbs and death. The compound is considered protective if there was an absence of a seizure for the entire observation period, Example 21

Minimal Clonic Seizure Test

Twenty CF-1 mice are pretreated with 30, 100 and 300 mg/kg test compound i.p. At varying times (0.25, 0.5, 1, 2, and 4 h) after treatment, individual mice (four at each time point) are administered eye drops of 0.5% tetracaine hydrochloride, and challenged with sufficient current (32 mA at 6 Hz for 3 s) delivered through corneal electrodes to elicit a psychomotor seizure. In general, this seizure is characterized by a minimal clonic phase, followed by stereotypy and automatistic behaviors described originally as being similar to the aura of human patients with partial seizures (Toman, *Neurology*, 1951. 1:444-460). Animals not displaying this behavior are considered protected.

Example 22

Hippocampal-Kindled Rat Test (Focal Seizures)

Electrodes are implanted into the hippocampus of anesthetized rats, which are then allowed to recover for 1 week. Following the rapid kindling protocol (Lothman et al., *Brain Res.*, 1994. 649:71-84), the rats are stimulated with 200 mA for 10 s, 50 Hz, every 30 min for 6 h on alternate days until they are fully kindled (4-5 stimulus days). After 1 week of rest, the animals are given the same electrical stimulus, which served as a baseline. The animals are pretreated with the test compound (by i.p. injection) and then tested at various intervals. At each time point, the behavioral seizure score and after-discharge duration are recorded. The behavioral seizure scores are scored according to the following criteria (Racine, *Electroencephalogr Clin Neurophysiol*, 1972. 32(3):281-94): stage 1—mouth and facial clonus; stage 2—stage 1 plus head nodding; stage 3—stage 2 plus forelimb clonus; stage 4—stage 3 plus rearing, and stage 5—stage 4 plus repeated rearing and falling. The after-discharge threshold (ADT) can also be measured in the kindled rat. The ADT is defined as the lowest current at which an after-discharge of at least 4 s is elicited. On the day of the test, the individual ADT of each rat is determined by increasing the current intensity in a stepwise fashion until the rat displayed an electrographic after-discharge with duration of at least 4 s. The initial stimulation is conducted at an intensity of 20 µA with 10 µA increments every 1-2 min until an after-discharge was elicited. Fifteen minutes after the predrug threshold determination, a single dose of the test substance is administered to 2 animals in a volume of 0.04 ml/10 g body weight. In this way, the animals serve as their own control. The individual rat ADT is then determined at varying times (i.e., 0.25, 1, 2 and 4 h) after drug administration. Results of this assay are presented in Table 2.

TABLE 2

| Compound | Rat |
|---|---|
| 3a | active at 200 mpk |
| 3c | active at 50 mpk |
| 3d | $ED_{50}$ 79 mpk |
| 8a | $ED_{50}$ 25 mpk |
| 10a | $ED_{50}$ 32 mpk |
| 16a | active at 100 mpk |

Example 23

In Vitro Spontaneous Bursting Model of Pharmacoresistance

Systemic Kainate (KA) Treatment: KA treatment consists of multiple systemic injections of KA in a modified protocol as previously described (Hellier, et al., *Epilepsy Research*, 1998. 31:73-84). Sprague-Dawley rats are removed from their home cages, weighed, and placed individually into Plexiglass tubs for injections and monitoring. Seizures are scored during the experiment based on the Racine scale (Racine, *Electroencephalogr Clin Neurophysiol*, 1972. 32(3):281-94). Vehicle (0.9% saline) or KA (5 mg/kg, i.p.) is administered once every hour until animals begin to exhibit behaviors consistent with early stage seizures (Stage 1-3). Once an animal has begun to seize, dosing is ceased or reduced to 2.5 mg/kg (i.p.) for that animal until at least one Stage 4/5 seizure per hour is observed. The number and stage of seizures is recorded until the animal has exhibited Stage 4 or Stage 5 seizures for 3.5 hours. Animals not having at least one Stage 4 or 5 seizure per hour are not included in the analysis. After 3.5 hours of monitoring, rats are given an i.p. injection of 0.9% saline (1-2 mL) for hydration and returned to their home cages. The combined entorhinal cortex/hippocampal slice is obtained from the rats under anesthesia with pentobarbitol (35 mg/kg). Following rapid decapitation, the brains are removed and placed for one minute in an ice-cold, oxygenated (95% $O_2$/5% $CO_2$), Ringer's solution containing, (in mM): Sucrose (125.0), KCl (3.0), $NaH_2PO_4$ (1.2), $MgSO_4$ (2.0), $NaHCO_3$ (26.0), glucose (10.0), and $CaCl_2$ (2.0) (Scharfman, *J Neurophysiol*, 1997. 78(2):1082-95). The brains are then blocked and glued, cortex down, to the chuck of a vibratome. Horizontal sections (400 µm) containing the entorhinal cortex and hippocampus are taken and placed in a holding chamber for at least one hour before commencing recording. The oxygenated Ringer's solution in the holding chamber, and for recording, has NaCl (126 mM) instead of sucrose, pH=7.4 and osmolarity of 300-310 mOsm.

Extracellular field potential recordings (at 31±1° C.) are made in Layer II of the medial entorhinal cortex (mEC) with borosilicate glass electrodes (3-6 MΩ) filled with normal Ringer solution or 3M NaCl. A concentric bipolar stimulating electrode placed in the angular bundle is used to elicit field potential responses. Signals are filtered at 3 kHz, sampled at 10 kHz, and acquired for computer storage using a Digidata 1440A AD Converter (Axon Instruments). Stimulus input/output (I/O) curves are determined to establish stable baseline responses and to determine threshold and maximal responses. Voltage pulses of 1-20 V are triggered using a stimulus isolator unit. Only slices that generate stable I/O responses throughout the baseline recording period are accepted. The extracellular solution is then switched to one containing 6 mM KCl and 0.1 mM $Mg^{2+}$ in order to elicit spontaneous, electrographic burst activity (SB).

Results obtained with the investigational substance are compared to those results obtained with "traditional" (e.g., phenytoin, carbamazepine) and "non-traditional" (e.g., retigabine) anticonvulsants. The dependent variables that are measured include frequency and duration of bursts in the presence and absence of AEDs. Compounds (100 µM) found to substantially block the spontaneous bursting at this concentration are considered efficacious. Results are compared by Student's t-test with statistical significance defined as p<0.05.

Example 24

Lamotrigine (LTG)-Resistant Amygdala-Kindled Rat Model

Two groups (LTG and vehicle-treated, n=8-10 rats/group) of male Sprague-Dawley rats (250-300 g) are stereotactically implanted with an electrode in the left amygdala (AP+5.7 mm, ML+4.5, DV+2.0 from intra-aural zero) under ketamine-xylazine anesthesia. Animals are then allowed to recover for one week before commencing kindling (Postma et al., *Epilepsia*, 2000. 41:1514-21). One hour prior to the kindling stimulation, rats receive a single i.p. dose of either vehicle (0.5% methylcellulose (MC)) or LTG (5 mg/kg in 0.5% MC). The kindling procedure consists of delivering a 200 μAmp stimulus (suprathreshold) daily until all animals in both treatment groups display consistent Stage 4 or 5 seizures, as scored by the Racine rating scale. One week after all animals are kindled, the animals receive a challenge dose of LTG (15 mg/kg, i.p.) before being stimulated to confirm the LTG sensitivity of the vehicle-treated control animals, as well as the LTG-resistance of the LTG-treated group. The animals are then allowed a washout of 3 days. On day 3 of the washout, the animals are pre-stimulated to ensure recovery of the fully kindled seizure. On day 4, rats in both treatment groups are challenged with a single dose of an investigational AED (the dose that produced minimal motor impairment (MMI)). Rats in both treatment groups are then challenged with the kindling stimulus at the pre-determined TPE of the investigational AED. When a drug treatment is observed to significantly lower seizure score and decrease afterdischarge, a dose-response study can be conducted. For this study, the ability of a candidate substance to reduce the afterdischarge duration (ADD) and seizure severity is quantitated by varying the dose between 0 and 100% effect. Results are expressed as the number of animals protected (i.e., not displaying a secondarily generalized limbic seizure) over the number of animals tested. The seizure score is analyzed by Mann-Whitney U-test and the ADD (±S.E.M.) is analyzed by Student's t-test, with $p<0.05$ determined to be statistically significant. The median effective dose and 95% confidence interval is then calculated by probit analysis.

Example 25

Focal Seizures in Corneal-Kindled Mice

Adult male CF-1 mice (n=8 per group, 18-25 g) are kindled to a criterion of 5 consecutive secondarily generalized seizures (Racine stage 4 or 5, according to the corneal kindling protocol previously described (Rowley et al., *Epilepsy Res*, 2010. 92(2-3): 163-69; Matagne et al., *Epilepsy Res*, 1998. 31(1):59-71). Twice daily, a 0.5% tetracaine hydrochloride solution is applied to each eye and the optic nerve is stimulated through corneal electrodes (3 mA, 60 Hz, 3 seconds). After receiving twice daily corneal stimulations, CF-1 mice typically reach the first Stage 5 seizure between approximately days 10-14. Twice daily stimulations continue for each mouse until that mouse has achieved the criterion of 5 consecutive stage 5 seizures, whereby it is considered "fully kindled". Fully kindled mice are then stimulated every-other to every 3 days until all other mice within the group reach the criterion of 5 consecutive Stage 5 seizures. Testing of investigational compounds commences at least 5-7 days after receiving the last stimulation. For identification studies 100 mg/kg, of the test compound is administered i.p. to five groups of 4 fully kindled mice per group. Mice in each group are then tested at various time points (0.25, 0.5, 1, 2, 4 hours) after drug dosing. Mice displaying a seizure score <3 are considered protected. The time point with the most animals protected is considered the time of peak effect (TPE) of the investigational compound. Quantitative differentiation studies may also be performed at the TPE. At least 3 doses, sufficient to produce between 0%-100% protection as previously determined in the above described identification studies, are evaluated in groups of 8-10 fully kindled mice. After testing, the corneal-kindled animals are returned to their home cage, and allowed at least 3-4 days between tests to "washout" any investigational compound after testing. The ability of an investigational drug to block the fully kindled behavioral seizure is suggestive of activity against secondarily generalized partial seizures. For quantification of protection in the corneal kindling model, the effective dose at which 50% of mice are protected ($ED_{50}$), the 95% confidence interval (95% C.I.), and the slope+S.E.M. are calculated using probit analysis.

Example 26

Pilocarpine Rat Model

Compounds are assessed for their ability to halt pilocarpine-induced convulsive status epilepticus (SE). To identify doses of drug to be used in the SE testing, acute motor impairment is assessed following the intraperitoneal (i.p.) administration of doses starting at 100 and 300 mg/kg. Individual Sprague Dawley rats are evaluated for acute toxicity over several time points following administration of test compounds. The results obtained from this initial study determine whether any dose adjustments are required. The behavior of the animals is observed closely and recorded over a four hour period. Routinely, a minimum number of four rats, two per dose are employed in this acute screen.

To determine if the test substance can halt acute pilocarpine-induced status an initial qualitative efficacy screen is performed. A challenge dose of pilocarpine (50 mg/kg) is administered i.p. and animals observed until the first convulsive (e.g., Stage 3, 4, or 5) seizure (time zero). The seizure severity is determined using the Racine scale. At this point a minimally toxic dose of the candidate drug is administered to a group of 8 male albino Sprague Dawley rats (150-180 g) via the i.p. route of administration. Efficacy is defined by the ability of an investigational drug to halt the further expression of pilocarpine induced convulsive seizures (e.g., Stage 3, 4, or 5). Compounds found to possess significant protection at time zero (time from the first stage 3, 4, or 5 seizure) may proceeded to further evaluation in the sustained status model. In this test, the investigational drug is administered 30 minutes after the first observed convulsive seizure. This is a more severe test of a candidate's ability to halt the induced status. Compounds found to possess significant activity may be advanced for quantification wherein the $ED_{50}$ and $TD_{50}$ and corresponding 95% confidence intervals are determined. A minimum of 4 doses with at least 8 rats per dose are utilized in the quantification study.

The compounds of Table 3 were tested in the pilocarpine assay (initial qualitative efficacy screen) and showed activity at the dose shown when administered after seizure onset (mpk=mg/kg).

TABLE 3

| Compound | Dose |
| --- | --- |
| 3a | 200 mpk |
| 3d | 450 mpk |
| 8a | 65 mpk |
| 10a | 65 mpk |
| 10f | 65 mpk |

Example 27

Frings Audiogenic Seizure (AGS) Susceptible Mice

Male and female Frings audiogenic seizure-susceptible mice (18-25 g) are used in this study. For each screening test, groups of 8 mice each are treated i.p. with varying doses of the investigational compound. At the time of peak effect as determined in the MES test (in CF-1 mice), individual mice are placed in a round plexiglass jar (diameter, 15 cm; height, 18 cm) and exposed to a sound stimulus of 110 decibels (11 kHz) delivered for 20 sec. Mice are observed for 25 sec for the presence or absence of hind limb tonic extension. Mice not displaying hind limb tonic extension are considered protected. The severity of a seizure may also be quantitated by assigning a numerical score to the observed response, e.g., no response—0; wild running for <10 sec—1; wild running for >10 sec—2; clonic seizure—3; forelimb extension/hind limb flexion—4; tonic seizure—5. The ability of a test substance to block audiogenic seizures can be quantitated by results collected from different doses with protection between 0% and 100% used to calculate an $ED_{50}$. The anticonvulsant activity of those test substances that afford protection in this model is quantitated and the $ED_{50}$ and the 95% confidence interval calculated by probit analysis.

Example 28

Soman Rat Model

Rats are surgically prepared with cortical electrodes to record brain electroencephalographic (EEG) activity one week prior to testing. On the day of test, the animals are attached to the recording equipment and EEG is recorded continuously. After baseline recording, the animals are pre-treated with the oxime HI-6 (125 mg/kg, i.p.) to reduce the immediate lethal effects of nerve agent challenge. Thirty min after HI-6, the animals are challenged with 180 µg/kg (s.c.) of the nerve agent soman and 1 min later they were administered 2.0 mg/kg atropine methyl nitrate (i.m.). This treatment regimen elicits continuous seizure activity within 5-8 min after soman challenge in 100% of animals tested. Both EEG and neuropathological techniques are used to assess the effectiveness of anticonvulsant treatment. At progressively longer treatment delay times (5 min, 20 min or 40 min) after seizure onset animals are administered standard medical countermeasures (0.45 mg/kg atropine sulfate admixed with 25 mg/kg 2-PAM, 2.2 mg/kg diazepam) along with the adjunct test drug. Dose-effect curves for anticonvulsant effectiveness are determined.

Example 29

Harmaline-Induced Tremor Assay

The harmaline-induced tremor assay is the primary preclinical model of induced tremor. Male ICR mice (10 weeks old) were used in this study. Mice were group housed in OPTI mouse ventilated cages. All animals remained group housed during the duration of the study. All mice were acclimated to the colony room for at least one week prior to testing. During the period of acclimation, mice were examined on a regular basis, handled, and weighed to assure adequate health and suitability. Mice were maintained on a 12/12 light/dark cycle. The room temperature was maintained between 20 and 23° C. with a relative humidity maintained between 30% and 70%. Chow and water were provided ad libitum for the duration of the study. In each test, animals were randomly assigned across treatment groups.

Ten mice were tested in each group. All compounds were administered by oral gavage at a dose volume of 10 mL/kg: Harmaline (30 mg/kg) was prepared in sterile saline and administered subcutaneously.

Propranolol HCl (10 mg/kg) was dissolved in sterile saline and administered i.p. 20 minutes prior to harmaline.

Test compounds were suspended in 0.5% methylcellulose and administered i.p. 20 minutes prior to harmaline.

Group housed mice were brought to the experimental room for at least 1 h acclimation prior to testing. Mice were injected with either sterile vehicle, propranolol, or test compound and placed in separate holding cages for 20 minutes following which mice were injected with harmaline (30 mg/kg) and placed inside the Tremor Monitor (San Diego Instruments, SDI) chamber for a 10 minute acclimation period. After habituation, tremor activity of the mice was measured for approximately 8 min. The recorded frequencies (1-64 Hz) of activity and the number of tremor events were captured electronically.

Data were analyzed by the tremor monitor software (San Diego Instruments) in a two part process. Using a Fast Fourier Transform (FFT), an output is provided showing the percentage of activity (energy) recorded at each frequency. A center frequency of activity between 14-15 Hz is chosen, along with a bandwidth of 10 Hz. Using these parameters, tremor events were tabulated as short, long, and total events. A long event is defined as being greater than 0.5 seconds in duration, and a short event as between 0.3 and 0.5 seconds in duration.

Data were analyzed by analysis of variance (ANOVA) followed by Fisher PLSD post-hoc analysis. An effect was considered significant if $p<0.05$. Statistical outliers that fell above or below 2 standard deviations from the mean in any of the three measures (short, long or total tremor events) were removed from the final analysis.

The compounds listed in Table 4 were tested in the harmaline assay and showed significant reductions in total tremors at the oral doses noted (mpk=mg/kg).

TABLE 4

| Compound | Dose |
| --- | --- |
| 8a | 50, 150 mpk |
| 10a | 5, 15, 50, 150 mpk |
| 11b | 15, 50 mpk |
| 14a | 50 mpk |
| 15a | 50 mpk |
| 16a | 50, 150 mpk |

The various embodiments described above can be combined to provide further embodiments. All U.S. patents, U.S. patent application publications, U.S. patent applications, foreign patents, foreign patent applications, and non-patent publications referred to in this specification and/or listed in the Application Data Sheet are incorporated herein by reference in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A method for treating a neurological condition of a subject having said neurological condition, wherein the neurological condition is essential tremor, epilepsy, status epilepticus or nerve agent exposure, comprising administering to the subject an effective amount of a compound having the following structure (A):

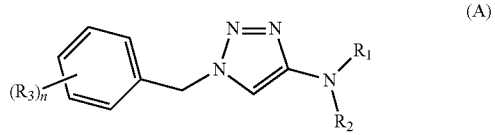

(A)

or a stereoisomer, ester, solvate, or pharmaceutically acceptable salt thereof,
wherein:
$R_1$ and $R_2$ taken together with the N to which they are attached, form a 5-6 member nonaromatic heterocycle wherein the 5-6 member nonaromatic heterocycle may be substituted with 0-3 $R_4$;
$R_3$ at each occurrence is Cl, F, $C_{1-4}$alkyl, —$OC_{1-4}$alkyl or trifluoromethyl;
$R_4$ at each occurrence is $C_{1-4}$alkyl; and
n is 0-3.

2. A method for treating a neurological condition of a subject having said neurological condition, wherein the neurological condition is essential tremor, epilepsy, status epilepticus or nerve agent exposure, comprising administering to the subject an effective amount of a pharmaceutical composition comprising a pharmaceutically acceptable carrier or diluent and a compound having the following structure (A):

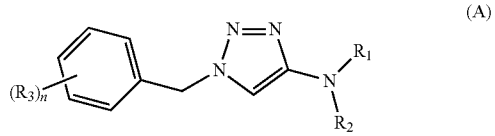

(A)

or a stereoisomer, ester, solvate, or pharmaceutically acceptable salt thereof,
wherein:
$R_1$ and $R_2$ taken together with the N to which they are attached, form a 5-6 member nonaromatic heterocycle wherein the 5-6 member nonaromatic heterocycle may be substituted with 0-3 $R_4$;
$R_3$ at each occurrence is Cl, F, $C_{1-4}$alkyl, —$OC_{1-4}$alkyl or trifluoromethyl;
$R_4$ at each occurrence is $C_{1-4}$alkyl; and
n is 0-3.

3. The method of any one of claim 1 or 2, wherein the neurological condition is essential tremor.

4. The method of any one of claim 1 or 2, wherein n is 1.

5. The method of any one of claim 1 or 2, wherein n is 2.

6. The method of any one of claim 1 or 2, wherein $R_3$ is Cl, F, or trifluoromethyl.

7. The method of any one of claim 1 or 2, wherein $R_3$ is $C_{1-4}$alkyl or —$OC_{1-4}$alkyl.

8. The method of any one of claim 1 or 2, wherein n is 1 or 2 and $R_3$ is F.

9. The method of any one of claim 1 or 2, wherein n is 1 and $R_3$ is F.

10. The method of any one of claim 1 or 2, wherein $R_4$ is absent.

11. The method of any one of claim 1 or 2, wherein n is 2 and each occurrence of $R_3$ is F.

12. The method of any one of claim 1 or 2, wherein $R_3$ is $C_{1-4}$alkyl, —$OC_{1-4}$alkyl, trifluoromethyl, or Cl.

13. The method of any one of claim 1 or 2, wherein the heterocycle formed by $R_1$ and $R_2$ taken together is piperidine.

14. The method of any one of claim 1 or 2, wherein the heterocycle formed by $R_1$ and $R_2$ taken together is morpholine.

15. The method of any one of claim 1 or 2, wherein the heterocycle formed by $R_1$ and $R_2$ taken together is piperazine, oxazolidine, or pyrrolidine.

16. The method of any one of claim 1 or 2, wherein $R_4$ is methyl or ethyl.

17. The method of any one of claim 1 or 2, wherein the compound is 4-{1-[(2,6-difluorophenyl)methyl]-1H-1,2,3-triazol-4-yl}morpholine.

18. The method of any one of claim 1 or 2, wherein the compound is 1-[(2,6-difluorophenyl)methyl]-4-(pyrrolidin-1-yl)-1H-1,2,3-triazole.

19. The method of claim 17, wherein the neurological condition is essential tremor.

20. The method of claim 18, wherein the neurological condition is essential tremor.

* * * * *